US011527318B2

(12) United States Patent
Theory et al.

(10) Patent No.: US 11,527,318 B2
(45) Date of Patent: Dec. 13, 2022

(54) METHOD FOR DELIVERING A DIGITAL THERAPY RESPONSIVE TO A USER'S PHYSIOLOGICAL STATE AT A SENSORY IMMERSION VESSEL

(71) Applicant: Sensync Inc., San Francisco, CA (US)

(72) Inventors: Alex Theory, San Francisco, CA (US); Adam Gazzaley, San Francisco, CA (US); James Jensen, San Francisco, CA (US)

(73) Assignee: Senkiva LLC, San Francisco, CA (US)

( * ) Notice: Subject to any disclaimer, the term of this patent is extended or adjusted under 35 U.S.C. 154(b) by 286 days.

(21) Appl. No.: 16/749,933

(22) Filed: Jan. 22, 2020

(65) Prior Publication Data

US 2020/0234814 A1    Jul. 23, 2020

Related U.S. Application Data

(60) Provisional application No. 62/795,468, filed on Jan. 22, 2019.

(51) Int. Cl.
*G16H 20/70* (2018.01)
*A61M 21/00* (2006.01)
*G06F 3/01* (2006.01)
*A61B 5/16* (2006.01)

(52) U.S. Cl.
CPC ............ *G16H 20/70* (2018.01); *A61B 5/165* (2013.01); *A61M 21/0094* (2013.01); *G06F 3/011* (2013.01)

(58) Field of Classification Search
CPC .... A61M 21/0094; A61M 21/02; A61G 10/00
See application file for complete search history.

*Primary Examiner* — Christine H Matthews
(74) *Attorney, Agent, or Firm* — Alpine Patents LLC; Brian Van Osdol

(57) ABSTRACT

One variation of a method for delivering a digital medicine experience to a user includes: loading the digital medicine experience at a sensory immersion vessel; calculating a target value of a bioindicator of the physiological state of the user, the target value of the bioindicator corresponding to a target physiological state of the user; at an initial time, rendering sensory representations of a set of elements in a multi-sensory virtual environment within the sensory immersion vessel at an initial progression rate; at a time during the digital medicine experience, succeeding the initial time, measuring a value of the bioindicator; calculating a progression rate through the digital medicine experience based on a difference between the value of the bioindicator and the target value of the bioindicator; and at a second time succeeding the time, rendering sensory representations of the set of elements in the multi-sensory virtual environment at the progression rate.

19 Claims, 5 Drawing Sheets

METHOD FOR DELIVERING A DIGITAL THERAPY RESPONSIVE TO A USER'S PHYSIOLOGICAL STATE AT A SENSORY IMMERSION VESSEL

CROSS-REFERENCE TO RELATED APPLICATIONS

This application claims priority to U.S. Provisional Patent Application No. 62/795,468, filed on 22 Jan. 2019, which is incorporated in its entirety by this reference.

TECHNICAL FIELD

This invention relates generally to the field of mixed reality and more specifically to a new and useful method for using a sensory immersion vessel and a user's physiological state to control a user's digital medicine experience in the field of mixed reality.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. First Method

Figure 1:
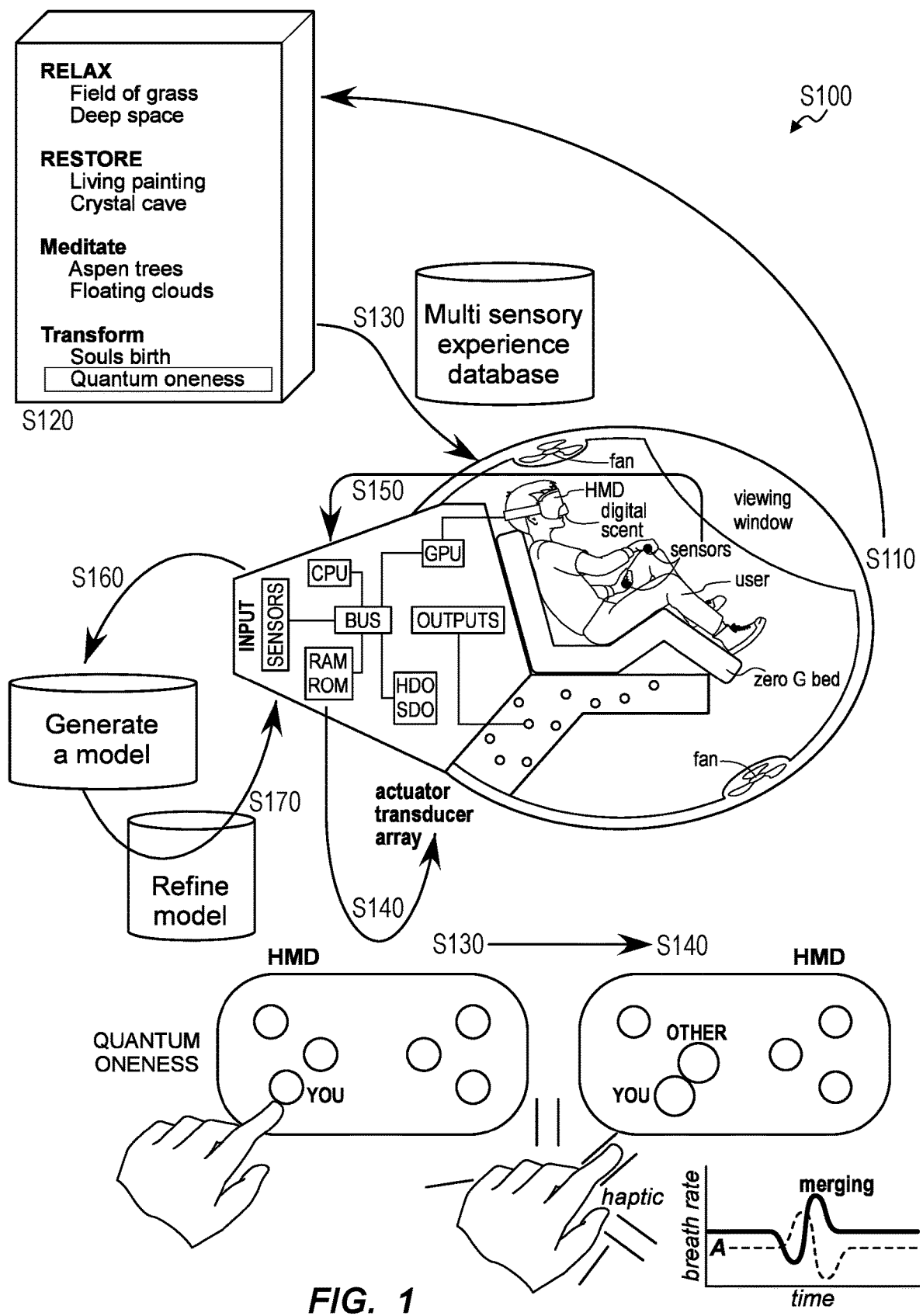
FIG. 1 is a flowchart representation of a first method.

As shown in FIG. 1, a method S100 of controlling a digital medicine experience (or "digital therapeutic experience") via a sensory immersion vessel (or "sensory modulation vessel" or "sensory modulation chamber") includes: presenting a set of digital medicine experiences that are controllable by the sensory immersion vessel in Block S110; obtaining a selection of a digital medicine experience in Block S120; engaging a user with the selected digital medicine experience through adjustment of a multi-sensory virtual environment and actuation of a set of sensory parameters by the sensory immersion vessel in Block S130; monitoring a physiological state of the user via physiological measurements during the selected digital medicine experience in Block S140; adjusting the digital medicine experience of the user based on the set of sensory parameters of the digital medicine experience and responsiveness of the physiological state of the user to the digital medicine experience in Block S150; generating a model for adjustments to the digital medicine experience based on the responsiveness of the physiological state of the user in Block S160; and refining the model based on the physiological state of the user and user feedback in Block S170.

As shown in FIG. 1, one variation of the first method S100 includes: monitoring the physiological state of the user in Block S140; adjusting the selected digital medicine experience for the user based on the sensory parameters of the digital medicine experience and the physiological state of the user in Block S150; generating a model based on the responsiveness of the physiological state of the user to adjustments made by the sensory immersion vessel in Block S160; acquiring feedback from the user following completion of the digital medicine experience in Block S170; and refining the generated model in Block S180.

Figure 2:
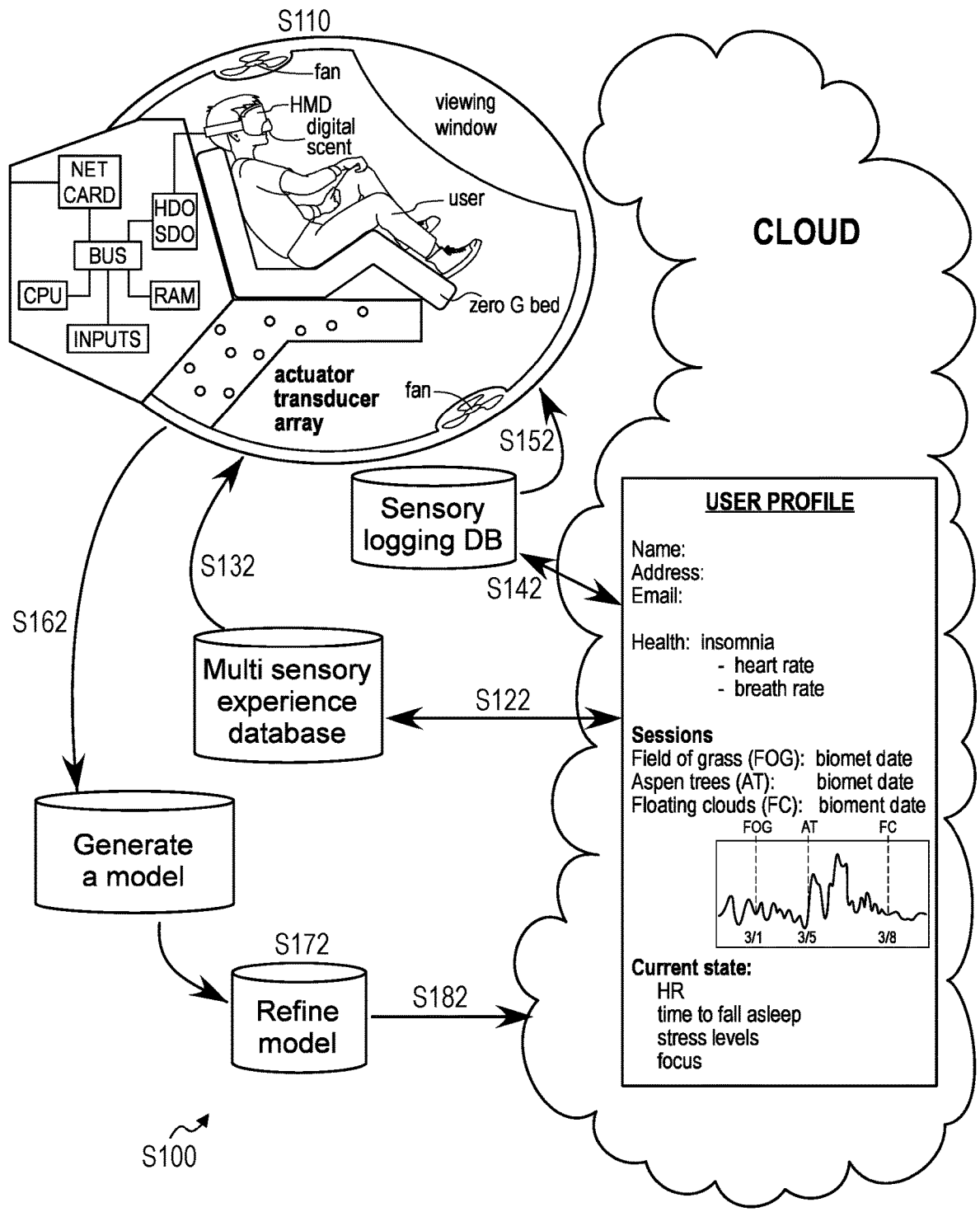
FIG. 2 is a flowchart representation of one variation of the first method.

As shown in FIG. 2, one variation of the first method S100 includes: presenting a user with a set of digital medicine experiences, controllable by the sensory immersion vessel, via an interface connected to an external computer system in Block Silo; obtaining a selection of a digital medicine experience based on a user profile in Block S122; engaging the user with the selected digital medicine experience through adjustment of the multi-sensory virtual environment based on information obtained from the external computer system in Block S132; monitoring the physiological state of the user in Block S142; adjusting the digital medicine experience based on the sensory parameters of the digital medicine experience and the information obtained from the external computer system in Block S152; generating a model based on the physiological state of the user and information obtained from the external computer system in Block S162; refining the model based on a user's physiological state or information from the external computer system in Block S172; and updating the digital medicine experience for an individual user or a population of users based on information stored in the external computer system in Block S182.

1.2 Applications

Generally, a sensory immersion vessel and/or an external computer system can execute Blocks of the first method S100 includes: serving a user with a set of available digital medicine experiences; delivering a digital medicine experience selected by the user; monitoring the user's physiological state via a set of physiological and/or biosensors integrated into the sensory immersion vessel; controlling a multi-sensory virtual environment and sensory parameters (e.g., visual, auditory, olfactory, haptic, tactile, proprioceptive) within the digital medicine experience in response to the user's physiological state; and developing a model that predicts changes in the user's physiological state responsive to such multi-sensory inputs, such as a model specific to the user or a user demographic, a model specific to the digital medicine experience, or a generic human or digital medicine experience model.

Blocks of the first method S100 can therefore be executed locally by the sensory immersion vessel or remotely by an external computer system that interfaces with the sensory immersion vessel. For example, the sensory immersion vessel and the external computer system can cooperate to: engage a user with a digital medicine experience based on content specific to the user (e.g., user profile data, demographic, previous experience, previous response, responsiveness to the digital medicine experience, context of use, user feedback etc.); monitor the physiological state of the user during, before, after, or between digital medicine experiences; adjust the digital medicine experience based on information obtained from the external computer system (e.g., current physiological measurements from the user); and generate, refine, and update the model based on information stored in the external computer system, including information specific to the user or information collected from multiple users of a sensory immersion vessel.

In particular, the sensory immersion vessel is configured to monitor the physiological state of the user by time series measurement of a physiological indicator or physiological measurement from the user, with the sensory immersion vessel controlling one or more features (or "channels," "modes") of the digital medicine experience in real-time during playback for the user based on the user's monitored physiological state in order to: transition the user toward a target physiological state defined by the digital medicine experience (e.g., relaxation, focus, meditation, energy boost); provide the user with an awareness of her present state in the context of the digital medicine experience by adjusting sensory representations of virtual objects within the experience (e.g., adjusting observable features of the multi-sensory virtual environment), including changing sensory parameters of the digital medicine experience and displaying hidden reveals or Easter eggs; and creating a closed loop system between the digital medicine experience and responsiveness of the physiological state of the user. The sensory immersion vessel (and/or the external computer system) further executes Blocks of the first method S100 to generate a model based on the responsiveness of a user's physiological state in response to the digital medicine experience. Additionally, the sensory immersion vessel can calculate a target physiological state for a user and monitor the physiological state of the user (e.g., average physiological state over a period of time, baseline physiological state before or after entering the sensory immersion vessel, physiological state at any given time during a digital medicine experience) relative to a target physiological state for the user. Once the target physiological state is attained, the sensory immersion vessel can display a hidden reveal or an Easter egg.

In one example, the sensory immersion vessel can implement Blocks of the first method S100: to present a user with a set of (e.g., one or more) digital medicine experiences that guide the user toward a target physiological state (e.g., relax, restore, meditate, transform) or toward target physiological metrics over one or more sessions in the sensory immersion vessel. The target physiological state or target metric for a single or set of digital medicine experiences is customized to information obtained by detecting the initial physiological state of the user and modulation of the transducers and actuators of the sensory immersion vessel to generate a multi-sensory virtual environment that stimulates the user's senses (e.g., auditory, tactile, visual, olfactory) and influences the physiological state of the user toward the target physiological state during the digital medicine experience. The sensory immersion vessel can generate time series data representing values of one or more physiological indicators throughout the digital medicine experience (e.g., user responsiveness to the multi-sensory virtual environment) and pair this time series with controlled multi-sensory outputs during the digital medicine experience in order to generate and refine a model predicting user responsiveness to stimuli within the multi-sensory virtual environment. Additionally, the sensory immersion vessel can be configured to detect the physiological state of the user between digital medicine experiences (e.g., when paired with a smartwatch or other wearable device) and prompt the user to start a digital medicine experience based on detection of the user's physiological state between the digital medicine experiences, thereby facilitating an efficient and effective digital medicine delivery routine for non-pharmaceutical cognitive enhancement.

1.2.1 Examples

Blocks of the first method S100 are described herein in the context of a sensory immersion vessel configured for operation with a user during isolated sessions (e.g., infrequent sessions with minimal user feedback). For example, the sensory immersion vessel can be installed in a hotel or spa for guests seeking relaxation. In this setting, a user may enter the sensory immersion vessel for a single session or a small number of consecutive sessions over a short period of time (e.g., during a vacation or an occasional visit to a spa). Accordingly, the sensory immersion vessel can account for such short-term usage and corresponding frequency to generate and adapt a model for the user by assessing the physiological state of the user during each individual session and/or customizing the model for the user based on an existing dataset for other users generated at the same or other sensory immersion vessel.

In another example, the sensory immersion vessel can be installed in an office space for use by office workers to improve focus and work performance. In this setting, a user may enter the sensory immersion vessel on a semi-regular basis over a longer period of time. The sensory immersion vessel can thus construct a model tailored to the performance of this specific user based on physiological data collected during digital medicine experiences completed by the user over this longer period time, and the sensory immersion vessel (or the external computer system) can account for other workplace-specific metrics or goals to generate and refine the user-specific model.

In yet another example, the sensory immersion vessel can be installed in a home for use by a user on a regular basis (e.g., daily, twice weekly, etc.), such as to reduce symptoms of a medical condition (e.g., insomnia, pain, etc.) or to address other symptoms. In this example, the sensory immersion vessel can: monitor the physiological state of the user during playback of digital medicine experiences for the user; monitor other symptom-specific feedback provided by the user; generate and refine a user-specific model that predicts a relationship between the user's physiological state or other physiological indicator data and the user's symptoms; and then implement this model to inform real-time modifications to subsequent digital medicine experiences responsive to real-time user physiological indicator data in order to reduce or control such symptoms. Therefore, in this example (and other examples), the sensory immersion vessel and/or the external computer system can: access a generic, condition-specific model generated from feedback and physiological state information of users; and then tailor this model to the specific user in order to link unique medical conditions or symptoms of the individual user (e.g., chronic pain, insomnia, stress, fatigue, and cardiac conditions) to the user's physiological state, user physiological indicator data, and outputs of the sensory immersion vessel.

1.3 Sensory Immersion Vessel

Figure 3:
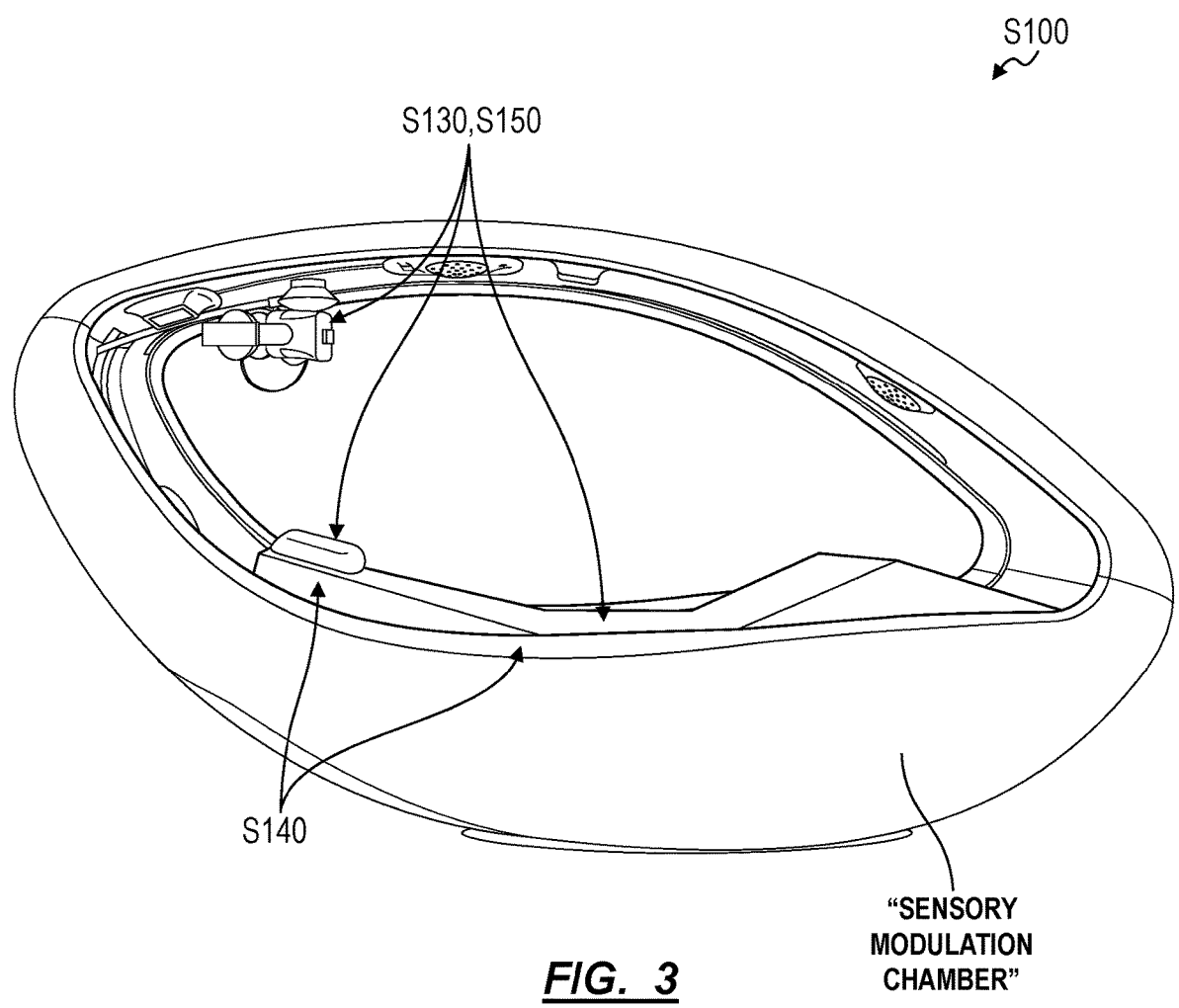
FIG. 3 is a schematic representation of one variation of the first method.

As shown in FIG. 3, the first methods S100 (and the second method S200 described below) can be implemented in conjunction with a sensory immersion vessel defining a semi-enclosed or fully-enclosed chamber housing a motorized and/or manually manipulatable zero-gravity bed configured to adjust to a variety of positions (e.g., lay flat, fully reclined, partially reclined, upright, etc.). The sensory immersion vessel further includes a set of displays such as a virtual/mixed reality headset (e.g., head-mounted display, heads-up display) and/or high resolution displays conformed to the interior surfaces of the sensory immersion vessel and facing the zero-gravity bed and configured to render an immersive, three-dimensional visual scene corresponding to a selected digital medicine experience. The sensory immersion vessel further includes a set of audio drivers including low-frequency vibroacoustic transducers for output of low frequency sound waves (e.g., to reproduce low-frequency sounds found in natural settings such as a rumbling waterfall) and high fidelity speakers for output of higher frequency sounds, music, audible prompts etc. The sensory immersion vessel further includes a set of tactile actuators, including fans for generating air movement within the enclosed vessel (e.g., at the head, torso, and/or foot sections of the sensory immersion vessel) and heating/cooling elements for adjusting the temperature within the sensory immersion vessel to represent various virtual objects within a multi-sensory virtual environment (e.g., the sun, cold water). In one variation, the sensory immersion vessel also includes a digital scent device (e.g., within a head set or head-mounted display device) configured to output olfactory representations of virtual objects within the multi-sensory virtual environment (e.g., perfumes with a grass scent, a redwood scent, or other customized scent).

The sensory immersion vessel also includes a set of physiological sensors configured to continuously and/or intermittently sample a set of bioindicators or physiological indicators representative of a physiological or mental state of the sensory immersion vessel's user throughout a digital medicine experience (e.g., in response to various sensory stimuli during the digital medicine experience). For example, the sensory immersion vessel can include a heart rate monitor that can be affixed to the user in order to sample the user's heart rate variability throughout a digital medicine experience, which can indicate a user's stress or excitation level. The sensory immersion vessel can also include a sensor configured to measure the user's rate of respiration and/or breathing rate variability throughout the digital medicine experience, which can further indicate a user's stress or excitation level. The sensory immersion vessel can also include a pulse oximeter that may be affixed to a user's finger in order to measure dissolved oxygen content or blood oxygen saturation levels throughout the digital medicine experience. The sensory modulation chamber can further include a set of electrodes that can be affixed to the user's skin in order to measure skin conductivity and/or galvanic skin response, which can indicate the user's level of stress/relaxation or other emotional responses to the digital medicine experience. In one variation, the sensory immersion vessel includes a set of EEG, EKG, or EMG electrodes arranged into a wearable headset or arranged within the AR/VR display headset described above, enabling the sensory immersion vessel or a computer interfacing with the sensory immersion vessel to continuously or intermittently monitor the user's brain waves/brain activity throughout the digital medicine experience, which can be interpreted by internal and/or external computer systems to determine the user's state of relaxation, meditation or excitation in response to the digital medicine experience.

Generally, the sensory immersion vessel includes and/or interfaces with a computing system including a central processing unit (CPU), graphical processing unity (GPU), hard drive/storage (cloud storage etc.), random access memory (RAM), a motherboard (e.g., input/output bus), and a network card configured to implement the first method S100 (and the second method S200 described below). In one implementation, the CPU, RAM etc. are located on board the sensory immersion vessel. In another implementation, these computing elements define a remote computer that interfaces with the sensory immersion vessel (e.g., using a wired or wireless connection) to implement Blocks of the first method S100 (and the second method S200).

1.4. Selection of Digital Medicine Experience

The computer system can present a user with a set of digital medicine experiences, such as selected from one of four (or more) categories designed to transition a user toward a particular target physiological state including: "relax" to engage the user with experiences that allow the user to relax both her mind and physical body and enjoy the sensations of the virtual environment; "restore" to renew focus/energy by distracting the user from stressors using a virtual environment configured to stimulate structure-free creativity; "meditate" to guide a user from an initial physical state (e.g., upon entering the sensory immersion vessel) toward a deep place of meditation that allows the user to be more mindful of the present moment; and "transform" to transition the user out of a state of ingrained individual awareness and transform the user's consciousness using a virtual environment and digital medicine experience that generates a connective unified field of consciousness experience for the user to operate within.

Therefore, the sensory immersion vessel receives a selection of a digital medicine experience including a multi-sensory virtual environment with sensory parameters that the sensory immersion vessel modulates and adjusts according to the user's physiological state and the user's responsiveness to the digital medicine experience. The user thus selects the digital medicine experience from a set of multi-sensory virtual environments, each of which fall within one of various categories (e.g., relax, restore, meditate, transform), each multi-sensory virtual environment provides a background context through which the user's senses are engaged by the digital medicine experience. Also, the external computer system can generate the digital medicine experience based on a selected physiological milestone and information stored in the external computer system, including information specific to the user or information collected from multiple users of a sensory immersion vessel. In particular, a digital medicine experience can define visual, auditory, olfactory, tactile, and proprioceptive sensory parameters in the context of a multi-sensory virtual environment, and the sensory immersion vessel can monitor the physiological state of the user during this digital medicine experience. Based on the visual, auditory, olfactory, tactile, and proprioceptive sensory parameters output by the sensory immersion vessel and time series physiological data collected by the sensory immersion vessel during the digital medicine experience, the sensory immersion vessel (or the external computer system) can identify correlations between the physiological state of the user and the magnitude/direction of sensory parameters of the multi-sensory virtual environment. Accordingly, the sensory immersion vessel can derive and implement a closed-loop feedback system between the user's physiological state and various individual parameters or groups of parameters within the digital medicine experience, such as including adjusting the magnitude and/or direction of these sensory parameters based on these correlations in order to transition the user from an initial physiological state toward a target physiological state—specified by the digital medicine experience or by the user—over the course of the digital medicine experience. Furthermore, the sensory immersion vessel can determine a target physiological state and modify the digital medicine experience to display a hidden reveal or Easter egg signifying to the user that the target physiological state has been attained.

In one example, the sensory immersion vessel receives a selection of a digital medicine experience under the relax category for an immersive virtual experience with the objective of allowing the user to relax within a "field of grass" environment. In this example the user is presented with the immersive digital medicine experience of soft rain while lying in a field of grass. Sensory parameters of the "field of grass" digital medicine experience include: visual presentation of a sequence of virtual reality frames including grass blowing in the wind below a set of slow-moving clouds; spatial auditory stimulation including sounds of soft rain and wind; olfactory stimulation including the smell of grass; a reclined or fully flat body position; and tactile stimulation including the pattering of rain, the subtle blowing of wind, and heat or cold from various objects (e.g., sun) in the environment. The sensory immersion vessel prompts the user via a message intended to guide the user to listen to the rain, slow down her physiological state, and notice the calmness of the environment. The sensory immersion vessel accordingly synchronizes sensory parameters to the user— for example the speed of the wind and/or the movement of the grass may be synchronized with the heart rate of the user. For the "field of grass" digital medicine experience, the sensory immersion vessel can define a target physiological state (e.g., target heart rate) for the user. Upon detecting that this target has been reached by the user during the digital medicine experience, the sensory immersion vessel can communicate this milestone, such as with an Easter egg, for example a rainbow appearing at the end of the digital medicine experience.

Alternatively, the sensory immersion vessel receives a selection under the relax category of a multi-sensory virtual environment with the objective of allowing the user to relax and enjoy the environment of "deep space". In this example, the user is presented with the immersive digital medicine experience of floating in deep space while slowly rotating. Sensory parameters of the "deep space" digital medicine experience include: visual presentation of a sequence of virtual reality frames including stars, luminescent nebulas, comets, and space dust; spatial auditory stimulation with sounds of space ambiance and relaxing tones; olfactory stimulation with a customized scent; a body position of laying down or reclining; and tactile sensations of passing through luminescence and nebulas. The user starts off with an object obstructing the user's view, possibly a planet or shadows of dark or light from the planet and, over the course of the experience, the user moves over the top of the object revealing a space-scape. The sensory immersion vessel synchronizes the sensory parameters (e.g., speed of luminescence between shadow and light) of the digital medicine experience with the physiological state of the user (e.g., with the heart rate of the user). For the "deep space" digital medicine experience, the sensory immersion vessel can define a target physiological state (e.g., heart rate) for the user. Upon detecting that this target has been reached by the user during the digital medicine experience, the sensory immersion vessel can communicate this milestone, such as with an Easter egg, a visualization of floating through a wormhole into another universe, or other hidden reveal.

In one example, the sensory immersion vessel receives a selection under the restore category of a "living painting" immersive virtual experience, in which the user is engaged in a creative structure-free environment configured to facilitate focus and cognitive enhancement. In this example, the sensory immersion vessel presents the user with the immersive digital medicine experience of floating through a vast open space in which the user's hands create various shares/textures/colors/sounds and scents. Sensory parameters of the "living painting" digital medicine experience include: visual presentation of a sequence of virtual reality frames including pulsing geometric objects, a dark or black environment with light particles, and amorphous nebulas; auditory stimulation including soothing music (e.g., customizable); olfactory stimulation including a custom scent; a body position or sensation of zero gravity; and tactile sensations including touch selection of objects and air movement to simulate direction related to the user's actions (e.g., painting and object placement). The user may experience floating toward the direction of the user's gaze (e.g., gaze-based navigation) with glowing orbs or attractors for the user to navigate between (e.g., orb to orb, or spline guidance) with selections appearing as the user floats forward in time. The sensory immersion vessel synchronizes the sensory parameters (e.g., rate of object pulsation) of the digital medicine experience with the physiological state of the user (e.g., with the respiration or breath rate of the user). For the "living painting" immersive virtual experience, the sensory immersion vessel can define a target physiological state (e.g., breath rate) for the user. Upon detecting that this target has been reached by the user during the digital medicine experience, the sensory immersion vessel can communicate this milestone, such as with an Easter egg, for example a zoom out that reveals to the user the entire painting that the user created.

Alternatively, the sensory immersion vessel receives a selection of a multi-sensory under the restore category titled "crystal cave". This selection has the objective of allowing the user to be engaged in a creative structure-free environment configured to facilitate focus and cognitive enhancement. In this example the user is presented with the immersive digital medicine experience of floating through a large cave filled with glowing crystals. Sensory parameters of the "crystal cave" digital medicine experience include: visual presentation of a sequence of virtual reality frames including caves with stalactites, stalagmites, glowing crystals and luminescent pollen; auditory stimulation including sounds of a cavern, echoes, water dripping, and auditory stimulation (e.g., customizable and/or soothing music); olfactory stimulation including a custom scent; a body sensation of zero gravity; and tactile sensations of seismic activity and air movement to indicate direction of movement. For example, the user may experience floating toward the direction of the user's gaze (e.g., gaze-based navigation) with glowing crystals or attractors for the user to navigate between (e.g., crystal to crystal, or spline guidance) with selections appearing as the user floats forward in time. The user may experience moving forward through the cave, navigation occurs from the user's movement from object to object (e.g., spline-based navigation) with new objects (e.g., stalactites, stalagmites, glowing crystals and luminescent pollen) revealed through the user's movement. The sensory immersion vessel synchronizes the sensory parameters (e.g., luminosity of the crystals) of the digital medicine experience with the physiological state of the user (e.g., breath rate or respiration rate of the user). For the "crystal cave" digital medicine experience, the sensory immersion vessel can define a target physiological state (e.g., target breath rate) for the user. Upon detecting that this target has been reached by the user during the digital medicine experience, the sensory immersion vessel can communicate this milestone, such as with an Easter egg, for example the experience of reaching a large cavern with a beam of sunlight shining on a mega crystal in the center of an iridescent pool of water.

In one example, the sensory immersion vessel receives a selection under the meditate category titled "aspen trees"—this experience has the objective of guiding the user from her initial state to a deep place of meditation that allows the user to rest or fall asleep. In this example, the sensory immersion vessel presents the user with the immersive digital medicine experience of trees and leaves moving in a rhythmic pattern. Sensory parameters of the "aspen trees" digital medicine experience controlled by the sensory immersion vessel include: visual presentation of a sequence of virtual reality frames including the bright yellow hues of aspen trees in autumn with flowing waterfalls and streams flowing; auditory stimulation including sounds of wind and flowing or falling water; olfactory stimulation including scents of aspens; a body sensation of zero gravity; and tactile sensations of the rumbling of wind and the sensation of wind on the skin of the user. Over the course of the digital medicine experience the sound gets quieter and birds and the sounds of trees fade, the waterfall may be accented with a glow and the rumble of the waterfall may increase. The sensory immersion vessel synchronizes the sensory parameters (e.g., speed of wind in the trees) of the digital medicine experience with the physiological state of the user (e.g., heart rate). For the "aspen trees" digital medicine experience, the sensory immersion vessel can define a target physiological state for the user. Upon detecting that this target has been reached by the user during the digital medicine experience, the sensory immersion vessel can communicate this milestone, such as with an Easter egg or hidden reveal.

Alternatively, the sensory immersion vessel receives a selection under the meditate category, of a digital medicine experience titled "floating clouds" with the objective of guiding the user from her initial state to a deep place of meditation that allows the user to rest or fall asleep. In this example the sensory immersion vessel presents the user with the immersive digital medicine experience of hovering in the sky far above the ground with clouds passing by and the sun setting on the distant horizon. Sensory parameters of the "floating clouds" digital medicine experience include: visual presentation of a sequence of virtual reality frames including blue sky, sunlight, clouds, and a green valley below; auditory stimulation including sounds of high altitude wind; olfactory stimulation with a custom scent; a body position of laying flat; and tactile sensations of passing through clouds with lower hanging clouds passing through the user and fans for direction. The user may experience the clouds drifting further apart to reveal open sky as the user progresses through the digital medicine experience. The sensory immersion vessel synchronizes the sensory parameters (e.g., movement of the clouds) of the digital medicine experience with the physiological state of the user (e.g., heart rate). For the "floating clouds" digital medicine experience, the sensory immersion vessel can define a target physiological state for the user. Upon detecting that this target has been reached by the user during the digital medicine experience, the sensory immersion vessel can communicate this milestone, such as with an Easter egg or hidden reveal.

In one example, the sensory immersion vessel receives a selection under the transform category, of a digital medicine experience titled "souls birth" with the objective of illustrating the connective and unified world that exists to the user through the experience. In this example the sensory immersion vessel presents the user with the immersive digital medicine experience of floating in darkness while hearing a heartbeat that gradually gets closer and louder. Over the course of the digital medicine experience the space presented to the user becomes increasingly illuminated revealing a womb pulsing with energy. Sensory parameters of the "souls birth" digital medicine experience include: visual presentation of a sequence of virtual reality frames including a womb, beating heart, amniotic sac, and a tunnel of light; auditory stimulation including sounds of heartbeat, blood pulsing, and ambient sounds inside/outside of a womb; olfactory stimulation including a custom scent; a flat body position; and tactile sensations including heartbeat and blood pulsing. The user may start with the experience of stillness being in a womb and over the course of the experience slowly drift or navigate from one object to another object (e.g., via spline-based navigation) toward a tunnel of light in the distance and move toward the light. The sensory immersion vessel synchronizes the sensory parameters (e.g., luminosity of veins/arteries) of the digital medicine experience with the physiological state of the user (e.g., breath rate or respiration rate). For the "souls birth" digital medicine experience, the sensory immersion vessel can define a target physiological state for the user. Upon detecting that this target has been reached by the user during the digital medicine experience, the sensory immersion vessel can communicate this milestone, such as with an Easter egg or hidden reveal, for example the experience of moving through a tunnel of light and emerging into total light.

Alternatively, the sensory immersion vessel can receive a selection under the transform category, of a digital medicine experience titled "quantum oneness" with the objective of illustrating the connective and unified world that exists to the user through the experience. In this example the sensory immersion vessel presents the user with the immersive digital medicine experience of floating in a vast abstract space with a representation of the user merging with other. Sensory parameters of the "quantum oneness" digital medicine experience include: visual presentation of a sequence of virtual reality frames including objects and characters as glowing particle systems that expand and contract as the viewer passes by them; auditory stimulation including sounds of beautiful music; olfactory stimulation including a custom scent; a body sensation of zero gravity; and tactile sensations of touching quantum objects and bodies and movement of air past the user as the user moves through space. The user may have sparse vocal guidance and commentary, with time speeding up and depiction of a zero-point energy field (e.g., quantum field of subatomic particles). The user is able to navigate freely between bodies and objects with interactions between the objects and generate a wave that interacts with other objects in the world. The sensory immersion vessel synchronizes the sensory parameters (e.g., luminosity of particle systems) of the digital medicine experience with the physiological state of the user (e.g., breath rate or respiration rate). For the "quantum oneness" digital medicine experience, the sensory immersion vessel can define a target physiological state for the user. Upon detecting that this target has been reached by the user during the digital medicine experience, the sensory immersion vessel can communicate this milestone, such as with an Easter egg or hidden reveal.

1.5 Presentation of Digital Medicine Experience

Block S120 of the first method S100 recites obtaining a selection of a digital medicine experience, which defines functions for modulating a set of sensory parameters synchronized to a multi-sensory virtual environment; and Block S130 of the first method S100 recites engaging a user with the selected digital medicine experience by adjusting the multi-sensory virtual environment and controlling actuators within the sensory immersion vessel according to the sensory parameters. Generally, in Block S120, when a selection of the digital medicine experience is made and then contained by the computer system, a model is loaded from hard drive storage, a solid-state drive, or from a profile on the cloud, such that they are loaded onto and accessible by the central processing unit to generate the digital medicine experience. The central processing unit (CPU) is connected to a motherboard internal to the sensory immersion vessel. The CPU and motherboard modulate outputs to change the sensory parameters that control an array of actuators/transducers that control the sensory parameters and modify the multi-sensory virtual environment by controlling a graphical processing unit (GPU) that renders the visual content on a head-mounted display.

The sensory parameters of the sensory immersion vessel are controlled by a motherboard/bus and CPU that are configured to actuate hardware in the sensory immersion vessel, including actuators and transducers that can produce auditory, olfactory, proprioceptive, or haptic sensations. Actuators/transducers include vibroacoustic transducers configured to emit low frequency sound vibration, digital scent actuators that can generate the effect of aromatherapy using digital inputs to produce sensory molecules or a digital signal that produces an olfactory response in the user, visually engaging displays (e.g., VR/AR headsets), speakers/amplifiers/sound generators, fans that can blow air in accordance with the direction of movement of the user or other observed effects (e.g., blowing of wind, etc.), and temperature elements that can create sensations of hot/cold in the multi-sensory virtual environment. Actuation may occur in synchronized concert with the animations and sensory experience, triggering activation of components in the sensory immersion vessel including fans, changes to seat position (e.g., lay flat, zero gravity, etc.), and movements made or experienced by the user.

The multi-sensory virtual environment is a reproduction of visual images produced by projection in virtual reality (e.g., in a VR headset, AR headset, head mounted display/HMD) or on a screen within the sensory immersion vessel. The multi-sensory virtual environment includes animations, hidden reveals (e.g., Easter egg experiences), and changes to the visual display that are synchronized with the physiological state of the user. In one implementation, the multi-sensory virtual environment is generated by the GPU and CPU in response to inputs received by the sensory immersion vessel, including inputs from sensors used to monitor the physiological state of the user. Alternatively, the GPU renders previously-recorded video content to the heads-up display. Previously-recorded content may be stored on a hard drive or streamed from the cloud through a network card with the motherboard/bus sending content to the GPU for rendering. In particular, frames of previously-recorded video may be rendered continuous by the dynamic assembly of the content based on the inputs received by the motherboard and in accordance with the machine-readable instructions stored locally, for example.

1.6 User Feedback

Block S140 of the first method S100 recites monitoring the physiological state of the user by recording the time series of a physiological indicator or physiological measurement synchronized with the digital medicine experience as a mechanism of obtaining direct feedback from a user in real-time. Shortly before or after entering the sensory immersion vessel, a user is connected to one or more sensors configured to record time series data for a physiological indicator or physiological measurement of the user. The sensory immersion vessel monitors the user's physiological state by measuring a physiological indicator or physiological measurement of the user inside the sensory immersion vessel; the sensory immersion vessel then generates a digital medicine experience for the user through actuation of hardware components of the sensory immersion vessel (e.g., lighting, fans, AR/VR headset, high resolution displays, vibroacoustic transducers, digital scent actuators, LEDs, speakers). In particular, throughout the digital medicine experience, the sensory immersion vessel: monitors various physiological indicators of the user based on outputs of biosensors integrated into the sensory immersion vessel; quantifies or qualifies a physiological state of the user based on these physiological indicators (or other physiological measurements) in Block S140; and modifies its sensory outputs during the playback of the digital medicine experience in order to move the user toward a target physiological state or in order to move the user along a target physiological trajectory specified by the digital medicine experience or elected by the user. Therefore, the sensory immersion vessel can implement closed-loop controls to adjust sensory outputs during the digital medicine experience in order to drive the user's current physiological state toward a target physiological state.

The sensory immersion vessel and/or an external computer system monitors a physiological indicator or physiological measurement that can include time series data providing an indicator of a physiological state for the user. A physiological measurement may include a heart rate (e.g., to gauge excitation and/or stress), EEG (e.g., to measure beta, alpha, theta, or delta states), skin sensors, pulse oximeters (e.g., for measuring dissolved oxygen levels), measures of respiratory rate, breath rate, skin conduction, heart rate variability, dissolved oxygen levels, and a physiological indicator may include combinations thereof (e.g., combinations of EEG and heartrate). A physiological indicator or physiological measurement is collected as the user enters the sensory immersion vessel, and an assessment is made based on a single variable or multiple variables used to establish a set of criteria. These criteria may be generalized to other users and used to customize the experience of users based on data collected from the single user.

Additionally, the sensory immersion vessel and/or an external computer system obtains feedback from the user asynchronously, for example at any time before, after, or between a single digital medicine experience or a set of digital medicine experiences (e.g., immediately or within a fixed time increment). For example, feedback may be obtained before the user enters the sensory immersion vessel using a questionnaire that assists the sensory immersion vessel and/or connected external computer system to customize the digital medicine experience for the user (e.g., to determine the model to use, characterization/classification of the user, to determine a target physiological state) and/or detect features of the physical state of the user that should be monitored in order to determine the user's physiological state and/or the user's response to the digital medicine experience. Feedback from the user may be obtained after the user's digital medicine experience. For example, the sensory immersion vessel may be configured to obtain contact information from the user and may contact the user directly after or within a defined duration after the digital medicine experience, in some non-limiting embodiments (e.g., for individuals using a sensor control chamber for personal and regular use at home, or in a work setting) the sensory immersion vessel is connectable (e.g., via API) with a wearable device or mobile device that provides feedback such as including ongoing physiological indicator or physiological measurements, target metric information, or other feedback that may be useful for determining the responsiveness of the user to the digital medicine experience(s) over time and between digital medicine experiences.

1.7 Modeling

Block S160 of the first method S100 recites using the sensory immersion vessel and/or an external computer system to generate a model based on a physiological state of the user with respect to the user's responsiveness to the multi-sensory virtual environment and actuation of a set of sensory parameters by the sensory immersion vessel; and Block S110 recites refining the generated model based on the physiological state of the user and the user's feedback. The model generated by the sensory immersion vessel can provide customized recommendations to the user based on the monitored physiological state of the user in her daily life through a connectable wearable or mobile device, as well as upon entering the sensory immersion vessel, with the model further adjusting the digital medicine experience based on the user's current physiological state and the responsiveness of the physiological state of the user to changes in the sensory parameters and the multi-sensory virtual environment. The sensory immersion vessel and/or an external computer system can further refine the model based on feedback obtained from the user (e.g., before, after, or between digital medicine experiences). Therefore, the sensory immersion vessel can use a model to estimate a target physiological state for the user (e.g., for a single digital medicine experience or over a course of digital medicine experiences) using feedback from the user and the user's physiological responsiveness to a digital medicine experience.

Additionally or alternatively, the sensory immersion vessel and/or an external computer system can generate a model for determining a target physiological state for a user and, when the target physiological state is attained, the sensory immersion vessel can: detect the physiological state for the user, compare the physiological state of the user with the target physiological state, identify that the physiological state of the user matches the target physiological state, and alter the digital medicine experience when an Easter egg or hidden reveal is presented to the user as part of the digital medicine experience. In one variation, a model is used to determine a target physiological state for a user based on: the selected digital medicine experience, the estimated duration or length of time of a multisensory experience, the initial physiological state of the user, and the responsiveness of the physiological state of the user as determined by previous digital medicine experiences. A sensory immersion vessel can combine demographic data with information derived from previous digital medicine experiences to generate a generalizable model capable of making recommendations for future digital medicine experiences for users that have never previously used the sensory immersion vessel.

Additionally or alternatively, models are generated in real-time based on a closed system feedback loop between the physiological state of the user measured by sensors in the sensory immersion vessel and the user's responsiveness to sensory parameters controlled by actuator/transistor output, for example as determined by absolute output of the actuators/transducers and/or the rate of change (e.g., actuator or transducer velocity) of the actuators/transducers in generating the digital medicine experience. The model is configured to close the loop and refine the sensory parameters or multi-sensory virtual environment of the digital medicine experience in real-time such that, over the course of the sensory experience, the user moves from an initial physiological state toward the target physiological state, attaining the target physiological state during the single digital medicine experience or over a course of several digital medicine experiences.

In one variation, the model is built from a single user's responsiveness to the absolute actuator/transducer output, with changes in the velocity of the actuator/transducer outputs for the individual user determined by comparison and labeling of the time series physiological data (e.g., physiological indicator or physiological state) from the user and the actuator/transducer outputs. A model may be built using a profile matrix representing features of the physiological state of the user and the responsiveness of the user to the sensory parameters that can be determined for a particular digital medicine experience or a set of digital medicine experiences, using a set of scores and weights representing a user's responsiveness to a magnitude or direction of the actuator/transducer outputs for each of the sensory parameters. In this variation, positive or negative correlations are established between the user's responsiveness and the actuator/transducer outputs, which are then used by the model to predict the impact of the actuator/transducer outputs on the physiological state for the single user. As recited in Block S110, the model is then refined in accordance with the physiological state received from the user. In this variation, the scores or weights are recomputed in response to new data, and the profile matrix is adjusted accordingly such that the model will result in different actuator/transducer outputs for moving the current physiological state of the user toward a target physiological state.

Alternatively, a real-time model generated for a single user may be generalized to a broader set of users using a library of user data. A library of user data for a set of users can be collected and stored (e.g., in a remote location, on a cloud or an external computer system) with user data labeled and processed based on one or more features including user demographic data, usage data, usage history, user feedback, and user's physiological state over time (e.g., physiological indicator or physiological measurements monitored over multiple digital medicine experiences and through connected wearable or mobile devices). Physiological states of the users (e.g., time series physiological indicator or physiological measurements) are analyzed (e.g., clustered, processed with FTT's or other signal processing methods) to identify correlations between the transducer/actuator velocity and/or absolute magnitude with the physiological state of the user. A set of user features may be identified and used to classify users to determine the model that applies to the user based on previous user data. Data within the library may be clustered and classified using methods known to those of skill in the art (e.g., supervised learning, unsupervised learning, neural net) to characterize a new user that has not had a previous digital medicine experience, or for an existing user (e.g., if they have few sessions and a low resolution model, if they are trying a new digital medicine experience for the first time, over time to accomplish a target physiological state). A model may be continually refined based on new inputs to the system, for example a model can be presented to the user for reassessment of the user's responsiveness in a single digital medicine experience or to recommend a course of digital medicine experiences. A user may be classified at the time of initiating a digital medicine experience according to classification of the user based on a library of previous user data, with the model recalculating and adjusting the digital medicine experience for the user in real-time according to the model selected during the classification.

In one variation, the sensory immersion vessel and/or an external computer system can modulate the physiological state of the user in real-time over the course of a digital medicine experience, based on a set of features extrapolated from the classification of the user according to the library of previous users. The library of previous user data may then be used to revise models stored in the sensory immersion vessel. Updates to the models can be made through direct upgrades of the models stored on the sensory immersion vessel (e.g., downloading from a transportable memory drives, changing onboard disks, etc.) or through interaction with an external computer system through a network connection.

In one variation, a sensory immersion vessel is customized for use as a reproducible research environment for controlled medical studies, for example using a sensory immersion vessel that is connected to a shared data system configured to interface with researchers. Block S120 of the first method S100 recites obtaining, either directly or indirectly, a selection of digital medicine experiences including the modulation of a set of sensory parameters and a multi-sensory virtual environment; for users engaging with the sensory immersion vessel in a research setting, the digital medicine experience may be selected by the researchers instead of by the user engaged with the digital medicine experience. In further embodiments, the first method S100 executes artificial intelligence models and a library of user data to train models for use by the sensory immersion vessel. For example, multiple types of physiological indicator or physiological measurement inputs and/or user feedback may be collected from users to build an extensive multi-parameter library of correlations between demographic information, user feedback, and physiological state with multi-sensory virtual environment and sensory parameter (e.g., actuator/transistor velocity and magnitude) data for use in research studies and/or to build testable cognitive models.

1.8 Variations

One variation of the first method S100 includes connecting the sensory immersion vessel to a user profile stored on a computer system external to the sensory immersion vessel. A user profile includes: the user's responsiveness to the digital medicine experience, the time series data plotting the physiological state of the user from the initial physiological state to a target physiological state, health data from medical records, knowledge about the types of digital medicine experiences that drive the user toward a target physiological state, demographic information, previous experiences, physical conditions, information regarding previous sessions including: session dates, session types, session durations, time series biometric data, time series physiological measurements, sensory parameters, multi-sensory virtual environments, actuator/transistor outputs, previously-used models, performance of models for the user, estimation for future performance based on the model, a prescribed session plan, user feedback, and the responsiveness of user to digital medicine experiences. In some instances, a user may be presented with a questionnaire before, after, or between digital medicine experience to generate user-specific recommendations for future or subsequent digital medicine experiences. This content may be stored in a user profile for access from a single or a set of sensory immersion vessels. In addition to a questionnaire, feedback from sensors in the sensory immersion vessel may collect information about the physiological state of the user. User information may be collected by wearable or portable devices and stored in the user's profile so that the sensory immersion vessel can monitor the status of the user before, between, and/or after sessions, and to prepare the user for a given digital medicine experience.

In one variation, a user's information is accessed from the user profile prior to the individual entering the sensory immersion vessel and combined with other user-specific information obtained from the sensory immersion vessel including the initial physiological state of the user (e.g., physiological state of the user at the time of entry into the sensory immersion vessel) and the selected digital medicine experience obtained by the sensory immersion vessel. Based on these inputs, a model is selected for engaging the user in the selected digital medicine experience. The user's responsiveness to the digital medicine experience, the time series measurement of the physiological state of the user, and the corresponding actuator/transistor data including absolute and velocity are then stored in the user profile.

In one variation a user is prompted to receive feedback from the user after the experience. Feedback is collected from a wearable or mobile device, including from a wearable device capable of collection physiological indicator or physiological measurements, through API connection to external databases for example databases containing work performance information, or from a post-journey questionnaire administered to the user for tracking one or more target metrics including symptom metrics like pain level or time to fall asleep. Feedback stored in the user profile and accessed by the sensory immersion vessel is then used for future experiences to accomplish target physiological states, target metrics (e.g., time to sleep, resting heart rate, etc., and to make recommendations for the types of digital medicine experiences that would help the user accomplish a defined target, or to prompt the user to return for a digital medicine experience based on the life-context and/or physiological state of the user between digital medicine experiences.

In one variation, a user uses the sensory immersion vessel semi-regularly in the context of a work setting; the user has a user profile with a history of digital medicine experiences and the responsiveness and physiological state of the user during the digital medicine experience. Between uses, the sensory immersion vessel monitors the physiological state of the user and the user's work obligations/performance using an API (application program interface) to incorporate access and integration with other smart devices. APIs are used to integrate the sensory immersion vessel with other devices that can provide notices and reminders to the user as well as provide feedback that can be used to make recommendations that prompt the user to return to the sensory immersion vessel. The physiological state of the user, feedback from the user, and API data is used to generate a model for supporting the user in attaining target metrics. For example, the sensory immersion vessel implements a model (e.g., AI model trained on previous data and feedback from the user) to selectively prompt the user to return to the sensory immersion vessel and receive a recommended digital medicine experience at a time that would be optimal (as defined by the model) for restoring the user to a target physiological state. The sensory immersion vessel is configured to engage the user over the course of a series of prompted and appropriately timed digital medicine experiences to reach a target metric that is sustained between the digital medicine experiences. A target metric can include a target physiological state, as well as other metrics including level of focus, relaxation (as gauged by the user through user feedback), and the amount of time it takes for the user to fall asleep.

Furthermore, a model for improving intra-experience performance of the user may be generalized for a group of users. For example, the model can incorporate demographic information about the users, feedback from the users, and information about the physiological state of the users, to build a model that is generalizable. The model can then be refined based on the continual collection of user data, including information obtained for a target metric or a target physiological state during each digital medicine experience and between digital medicine experiences.

2. Second Method

Figure 4:
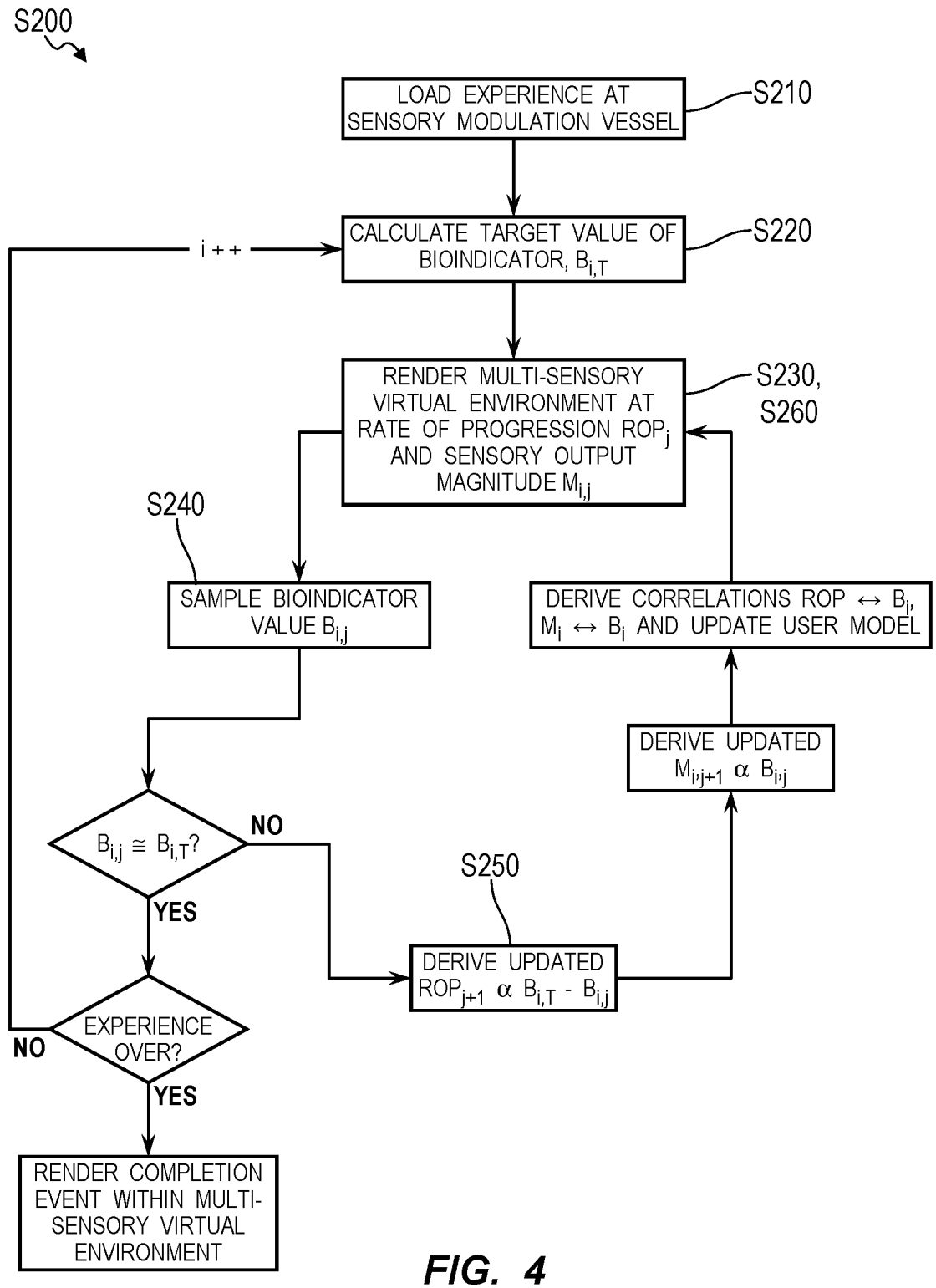
FIG. 4 is a flowchart representation of a second method.

As shown in FIG. 4, a second method S200 for delivering a digital medicine experience (or "digital medicine experience") responsive to a physiological state of a user of a sensory immersion vessel (or "sensory modulation vessel," "sensory modulation chamber") includes: loading the digital medicine experience at the sensory immersion vessel at Block S210; calculating a target value of a first bioindicator corresponding to a target physiological state of the user at Block S220; at an initial time, rendering sensory representations of a set of elements in a multi-sensory virtual environment within the sensory immersion vessel at an initial rate of progression at Block S230; at a first time during the digital medicine experience, succeeding the initial time, sampling a first value of the first bioindicator at Block S240; calculating a first rate of progression through the digital medicine experience based on a first difference between the first value of the first bioindicator and the target value of the first bioindicator at Block S250; and, at a second time succeeding the first time, rendering sensory representations of the set of elements in the multi-sensory virtual environment at a first rate of progression at Block S260.

2.1 Applications

Generally, the method S200 can be implemented by the sensory immersion vessel described above and/or by a local or external computer connected to the sensory immersion vessel (hereinafter the "system") to: render a multi-sensory virtual environment for a user (e.g., occupant) of the sensory immersion vessel during a digital medicine experience; monitor a set of biosignals representing the user's physiological state (e.g., heart rate, breathing rate, galvanic skin response) at a set of sensors within the multi-sensory virtual environment during the digital medicine experience; derive correlations between sensory stimuli in the multi-sensory virtual environment and changes in the set biosignals observed (e.g., measured, sampled, recorded) during the digital medicine experience; and adjust sensory parameters of the multi-sensory virtual environment based on sampled values of the set of biosignals and/or the derived correlations to guide the user into a target physiological state according to therapeutic goals of the digital medicine experience. Thus, the system can execute Blocks of the second method S200 to render an immersive multi-sensory virtual environment (e.g., a natural setting) within the sensory immersion vessel that is responsive to, dependent on, and partially controlled by the physiological state of the user (e.g., as measured by the set of bioindicators) and/or the physiological state of the user relative to a target physiological state for the experience. More specifically, the system can adjust (e.g., dynamically recalculate) a rate of progression through the experience (e.g., the user's perceived rate of movement through the multi-sensory virtual environment) and sensory representations of objects in or features of the multi-sensory virtual environment according to measured values of these biosignals and predicted physiological responses of the user to these stimuli in a closed loop control system in order to guide the user into a target physiological and/or neurological state (e.g., low heart rate, minimal stress responses, increased relaxation, increased alertness) during the course of the experience.

Thus, the system can customize a mixed-reality experience to the physiology of a user in real time in order to effect physiological and/or neurological changes within the user toward specifically targeted physiological and/or cognitive states associated with specific therapeutic goals, thereby promoting real-world cognitive and behavioral benefits for the user, such as increased relaxation, reduced stress or anxiety levels, reduced insomnia or jetlag, meditation, and/or increased focus or alertness (e.g., over multiple therapies at the sensory immersion vessel). For example, upon detecting that the user has achieved the target physiological state for the experience (or during subsequent experiences) the system can gradually increase the level (e.g., magnitude) of sensory stimuli in the multi-sensory virtual environment while monitoring a particular biosignal or set of biosignals such as heart rate or galvanic skin response for reduced correlation with these stimuli. Over the course of the digital medicine experience or multiple consecutive digital medicine experiences, the second method S200 can condition the user to become less physically and/or mentally responsive to various sensory outputs or events within the multi-sensory virtual environment and to disassociate these responses from external stimuli, leading to a lasting reduction in the user's stress and anxiety levels in real-world environments.

Additionally, over the course of the digital medicine experience or multiple consecutive digital medicine experiences, the sensory immersion vessel can execute Blocks of the second method S200 to condition the user to become more physically and/or mentally responsive to particular sensory outputs or events within the multi-sensory virtual environment and to experience these outputs as positive cues to elicit the user's desired changes in cognitive functioning and/or mental state (increased focus, increased relaxation, reduced stress, etc.).

Furthermore, the sensory immersion vessel is an enclosed environment that can provide a consistent, replicable multi-sensory environment across multiple experiences and for multiple users, allowing the system to sample accurate physiological measurements and generate models of a user's physiological responses to controlled stimuli. Thus, the system can be employed as a diagnostic tool to provide accurate baseline physiological measurements of a user's resting heart rate, resting breathing rate, dissolved blood oxygen, blood pressure, EKG, EEG, skin responses etc. and avoid the effects of external stressors on these measurements that may arise in a hospital or other traditional medical environment. Moreover, the system can render a closed, consistent, and immersive environment that can enhance (e.g., complement) the delivery and/or help to evaluate the efficacy of various classes of pharmaceuticals, such as anti-anxiety medications, sleeping pills, or attention-enhancing drugs. The system therefore provides a digital medicine delivery device for both non-pharmaceutical and pharmaceutical-supplemented cognitive enhancement therapies.

2.2 Initialization

Blocks of the second method S200 recite: loading the digital medicine experience at the sensory immersion vessel at Block S210. Generally, the system is configured to: receive a selection of a digital medicine experience out of a set of available digital medicine experiences from a user; and access a physiological model of the user, a physiological model of one or more demographics associated with the user, and/or a model of the selected digital medicine experience predicting how the user may respond physiologically and/or neurologically to the selected digital medicine experience.

Prior to initiating a digital medicine experience within the sensory immersion vessel, the system receives a selection of a digital medicine experience from a set of available experiences (e.g., a set of 32 distinct digital medicine experiences). For example, the user may select a digital medicine experience from one of four categories: "relax," which includes experiences that calm the user and bring her to a resting physiological state (e.g., to distract from external stressors, prepare for sleep); "restore," which includes interactive, engaging experiences with active user participation in order to increase focus and energy levels; "meditate," which includes experiences that guide the user into a meditative mental state; and "transform," which includes experiences designed to bring the user out of her current headspace and broaden her environmental and psychospiritual awareness.

In one implementation, the system presents the user with information on each category of digital medicine experience and displays available experiences within each category (e.g., on a tablet computer paired with the sensory immersion vessel, on a smartwatch paired with the sensory immersion vessel). For example, the user may then directly select a desired digital medicine experience from the menu of available experiences by selecting an affordance on a portable computer paired with the sensory immersion vessel. In another implementation, the system issues an initial survey to the user on a portable electronic device paired to the sensory immersion vessel and subsequently recommends a digital medicine experience to the user based on her responses. For example, the survey may ask the user to enter basic demographic and/or medical information (e.g., age, gender, weight, known medical conditions), her goals for the experience (e.g., get ready for bed, increase focus), and any preferences regarding the setting of the experience (e.g., a natural environment, a space environment). The system can then: analyze the user's responses to the initial survey; determine which digital medicine experience in the set of available experiences most closely aligns with the user's current preferences and/or medical limitations; display information regarding the recommended experience on a portable electronic device paired to the sensory immersion vessel; and receive confirmation from the user selecting the recommended digital medicine experience at the portable electronic device. For example, if the initial survey indicates user preferences consistent with the "relax" category, that the user would prefer a natural setting for her digital medicine experience, and that the user is not claustrophobic, then the system can recommend the "crystal cave" experience, display information regarding the "crystal cave" experience at a tablet computer paired with the sensory immersion vessel, and prompt the user to confirm selection of the "crystal cave" experience at an affordance displayed on the tablet.

Upon receiving selection of a desired digital medicine experience, the system can access a physiological model of the user, a physiological model of one or more demographics associated with the user, and/or a physiological model of the selected digital medicine experience (e.g., from cloud storage). For example, if the user has previously had a digital medicine experience at the sensory immersion vessel or a similar sensory immersion vessel, then the system can access a physiological model of the user generated during and/or her previous experiences. The physiological model of the user may include and/or be based on a set of time series data representing a set of bioindicator values showing her physiological and/or neurological responses throughout previous digital medicine experiences administered at the sensory immersion vessel, as well as sensitivities of these bioindicators (e.g., the user's physiological sensitivities) to various sensory stimuli (e.g., visual stimuli, auditory stimuli, tactile stimuli) that may be output during the selected digital medicine experience. For example, the physiological model of the user may include time series representations of her heart rate, respiration rate, galvanic skin response, and brain activity (e.g., measured by EEG) sampled throughout her previous digital medicine experiences within the sensory immersion vessel, as well as any changes in these bioindicators that occurred in response to controlled visual stimuli, auditory stimuli, tactile stimuli, etc. (e.g., biosensitivities) issued during previous digital medicine experiences or in response to certain events that occurred within the multi-sensory virtual environment during these experiences. The physiological model of the user may also include predictions of the user's physiological responses to stimuli, events, or other controllable parameters (e.g., rate of movement through the multi-sensory virtual environment) within the selected digital medicine experience derived from the time series of these bioindicators and corresponding biosensitivities. If a physiological model of the user is not available (e.g., in the case of a first-time user), the system can instead access physiological models of users who share one or more demographics with the user as indicated by the initial survey. For example, the system can access physiological models of women between the ages of 40 and 50 in response to receiving an initial survey indicating that the current user shares these demographic criteria. Additionally and/or alternatively, the system can access models specific to the selected digital medicine experience (e.g., generated across all users who have had the selected experience, generated across users who share common demographics with the current user who have had the selected experience).

The system can then determine initial sensory parameters of a multi-sensory virtual environment corresponding to the selected digital medicine experience based on the physiological model of the user, the physiological model of the user's demographic, the physiological model of the selected digital medicine experience, and/or current baseline physiological measurements (e.g., current heart rate, current rate of respiration) taken by the sensory immersion vessel.

2.3 Baseline and Target Physiological States

Blocks of the second method S200 recite: calculating a target value of a first bioindicator of the physiological state of the user, the target value of the first bioindicator corresponding to a target physiological state of the user at Block S220. Generally, the system is configured to: sample baseline (e.g., current, initial) values of a set of bioindicators (e.g., heart rate, rate of respiration, galvanic skin response, brain activity, etc.) at a set of sensors within the sensory immersion vessel prior to initiating the digital medicine experience; determine a target physiological state for the user based on her selected digital medicine experience, baseline values of the set of bioindicators (e.g., current physiological state), and/or the physiological models of the user and/or the user's demographic; and calculate a target value of a particular bioindicator (e.g., heartrate) representing the target physiological state and defining a target physiological metric.

Generally, the system is configured to obtain a set of baseline physiological measurements from the user (e.g., bioindicator values) prior to initiating the digital medicine experience. Thus, upon entering the sensory immersion vessel, the user interfaces with a set of physiological sensors within the sensory immersion vessel to allow intermittent sampling and/or continuous monitoring of a set of bioindicators representing the user's physiological and/or mental state both prior to beginning and throughout the progression of the digital medicine experience. For example, the user may wear a headset (e.g., a custom AR/VR headset) that includes a breathing monitor (e.g., to measure rate of respiration), pulse oximeter to allow the system to sample her heart rate and dissolved blood oxygen levels, and a set of EEG electrodes to monitor the user's brain activity before and during the digital medicine experience (e.g., to measure alpha, beta and theta brainwaves). Prior to initializing the digital medicine experience (e.g., prior to rendering the multi-sensory virtual environment corresponding to the selected experience), the system can recruit the set of physiological sensors to sample baseline (e.g., initial) measurements of the user's heart rate, respiration rate, blood pressure, galvanic skin response, dissolved blood oxygen and/or brain activity, which may indicate the user's current degree of stress, state of relaxation/excitation, etc. Furthermore, at any time during the experience, the system can recruit the set of physiological sensors to sample baseline (e.g., initial) measurements of the user's heart rate, respiration rate, blood pressure, galvanic skin response, dissolved blood oxygen and/or brain activity, which may indicate the user's current degree of stress, state of relaxation, degree of excitation, etc.

The system can then determine (e.g., derive, compute, set) a target physiological state for the user to reach during the digital medicine experience. In one implementation, the system determines the target (e.g., goal) physiological state based on the digital medicine experience selected by the user. For example, if the user has selected the "crystal cave" experience in the "relax" category, the system may set a target physiological state including a low rate of respiration (e.g., indicating deep breathing), the resting heart rate of user, and a small galvanic skin response (e.g., indicating minimal stress response). In another example, the target physiological state includes and/or defines specifically targeted neurological and/or cognitive states associated with a therapeutic goal of the digital medicine experience (e.g., according to bioindicators such as brain activity), such as increased relaxation, reduced stress, increased alertness, etc.

Subsequently and/or concurrently, the system can derive (or estimate, calculate) target values for these bioindicators for achievement by the user during the digital medicine experience based on a physiological model of the user and/or physiological models of the user's demographic. For example, the system can access time series data representing heart rate, breathing rate, and galvanic skin response sampled from the user during her previous digital medicine experience in the same category and set a target heart rate, target breathing rate, and/or target galvanic skin response for the current digital medicine experience to be less than or equal to the lowest value of each bioindicator observed in the previous experience. In another example, the system can access heart rates, breathing rates, and/or galvanic skin responses attained by other users at the end of the selected digital medicine experience from physiological models of previous users in a similar demographic. For example, the system can then derive the target heart rate, target breathing rate, and/or target galvanic skin response for the current user to be equal to an average of these values. In one implementation, the system derives a target value for a particular bioindicator to account for the initial value of this bioindicator measured by the sensory immersion vessel prior to initializing the digital medicine experience in order to tailor target physiological metrics to the user's current physiological state. For example, if the user's baseline physiological state upon entering the sensory immersion vessel indicates particularly high stress levels (e.g., high galvanic response, brain activity indications), the system can adjust the target heart rate to a higher value in accordance with observed bioindicator values. The system can therefore derive and set a target physiological state (e.g., including a targeted neurological state) and target bioindicator values—for achievement by the user—during the digital medicine experience that are both appropriate for the user's physiology and physiologically consistent with the therapeutic goal of the selected experience (e.g., "relax," "restore").

In another implementation, the system derives an updated target value for a particular bioindicator to account for a value of this bioindicator sampled (e.g., measured) by the sensory immersion vessel at any time during the course digital medicine experience in order to tailor target physiological metrics to the user's current physiological state. For example, if the user's physiological state at a later time during the digital medicine experience indicates particularly high stress levels (e.g., high galvanic response, brain activity indications), the system can adjust the target heart rate to a higher value in accordance with observed bioindicator values. The system can therefore derive and set an updated target physiological state and target bioindicator values for the user to reach during the digital medicine experience that is responsive to the user's physiology and physiologically consistent with the therapeutic goal of the selected experience (e.g., "relax," "restore").

2.4 Multi-Channel Stimulus Presentation

Blocks of the second method S200 recite: at an initial time, rendering sensory representations of a set of elements in a multi-sensory virtual environment within the sensory immersion vessel at an initial rate of progression at Block S230. Generally, the system is configured to: render a sequence of mixed reality frames representing a multi-sensory virtual environment corresponding to a selected digital medicine experience in the sensory immersion vessel, including rendering visual objects on a set of displays within the sensory immersion vessel and synchronously outputting auditory, tactile and olfactory representations of objects in and/or features of the multi-sensory virtual environment; calculate an initial or current rate of progression and/or movement through the multi-sensory virtual environment based on the initial or current physiological state of the user and/or physiological models of the user or the user's demographic; and advance through the sequence of mixed reality frames representing the multi-sensory virtual environment at the initial rate of progression at the start of the digital medicine experience or at the current rate of progression.

Upon initiating the digital medicine experience, the sensory immersion vessel is configured to render a sequence of mixed reality frames including visual, auditory, tactile/haptic, and olfactory representations of objects (e.g., virtual objects) in an immersive multi-sensory virtual environment corresponding to the selected digital medicine experience. In particular, the system is configured to, at the initial time, render a set of visual objects in the multi-sensory virtual environment at a display or set of displays (e.g., an AR/VR headset, a heads-up display, high resolution displays conformed to interior surfaces of the sensory immersion vessel). In the example of the "crystal cave" experience, rendering the set of visual objects includes rendering three-dimensional visual representations of a body of still water in an open subterranean cavern, stalactites suspended from the cavern ceiling, and stalagmites emerging from the water such that the user perceives herself as floating through the air near or above the water while observing her surroundings. The sensory immersion vessel also renders and animates set of crystal formations located throughout the cave such that they appear to glow and pulse (e.g., grow alternately brighter and dimmer) with light of a particular color. As discussed in more detail below, the system can correlate rendering and/or animation of these visual objects in the multi-sensory virtual environment with a particular bioindicator as measured by sensors within the sensory immersion vessel in order to deliver a digital medicine experience that simultaneously responds to and influences the physiological and/or neurological state of the user. For example, the sensory immersion vessel can render (e.g., animate) the crystal formations within the cave to pulse at a rate (e.g. increase or decrease in luminosity) proportional to the user's rate of respiration, which may both increase the user's immersion in the multi-sensory virtual environment and implicitly guide the user toward the target rate of respiration.

Concurrently (e.g., at the initial time), the sensory immersion vessel is configured to output (e.g., render, play back, generate) a set of auditory signals corresponding to a subset of visual objects in and/or features of the multi-sensory virtual environment at a first set of actuators within the sensory immersion vessel. In one implementation, the sensory immersion vessel is configured to output low frequency sound waves corresponding to objects and/or features of the multi-sensory virtual environment at a set of low frequency vibroacoustic transducers and to output higher frequency audio signals (e.g., sound effects corresponding to other objects/features of the multi-sensory virtual environment, music) at a set of higher range speakers. In the example of the "crystal cave" experience, the sensory immersion vessel may output (e.g., play back) low frequency sounds at the low frequency vibroacoustic transducers to generate an ambient, subterranean soundscape within the sensory immersion vessel. Concurrently, the sensory immersion vessel may output higher frequency sounds at the set of speakers representing the sound of flowing water, water dripping from stalactites into a pool below, a gentle wind and/or a humming or other custom sound effect representing the pulsing crystal formations. Generally, the sensory immersion vessel can synchronize the auditory representations of these objects or features of the multi-sensory virtual environment with visual renderings on the display(s) in the sensory immersion vessel in order: to increase the user's perception of immersion in the multi-sensory virtual environment; and to facilitate the user's transition to the target physiological state. Thus, by synchronizing sensory outputs across multiple sensory modalities (e.g., sensory synchronization) and customizing the digital medicine experience to the physiological state of the user according to the closed-loop controls described below, the system can deliver experiential treatments through which a user may achieve a meaningful and sustainable health benefit.

The sensory immersion vessel is further configured to concurrently (e.g., at the initial time or at a later time during the experience) output (e.g., render, play back, generate) tactile representations of a second subset of visual objects or features of multi-sensory virtual environment at a second set of actuators within the sensory immersion vessel. Outputting tactile representations of objects within or features of the multi-sensory virtual environment can include: generating air movement within the sensory immersion vessel at a set of fans within the sensory immersion vessel, generating movement of or vibration in the zero gravity bed within the sensory immersion vessel; and generating heating or cooling within portions of the sensory immersion vessel at a set of heating and cooling elements within the sensory immersion vessel. In the example of the "crystal cave" experience, the zero-gravity bed within the sensory immersion vessel is reclined to a flat (e.g., horizontal) position at the start of the digital medicine experience and actuated to Zero G position to simulate a sensation of floating through the air. The system can also actuate a set of fans in the sensory immersion vessel to generate air movement within the head, torso, and leg/foot sections of the sensory immersion vessel, representing a slight breeze through the cavern which may be proportional to a perceived rate of movement through the cave (e.g., as rendered on the set of displays within the sensory immersion vessel). Generally, the system synchronizes output of tactile representations of particular objects in or features of the multi-sensory virtual environment with visual and/or auditory representations of these objects/features at other actuators within the sensory modulation vessel in order to increase the user's immersion within the multi-sensory virtual environment and facilitate the user's transition from her baseline physiological state to the target physiological state during the digital medicine experience. Thus, by synchronizing sensory outputs across multiple sensory modalities (e.g., sensory synchronization) and customizing the digital medicine experience to the physiological state of the user according to the closed-loop controls described below, the system can provide effective experiential treatments through which a user may achieve a meaningful and sustainable health benefit.

The sensory immersion vessel is further configured to concurrently (e.g., at the initial time) output olfactory representations of a third subset of visual objects in or features of the multi-sensory virtual environment at a third set of actuators within the sensory immersion vessel. In particular, the sensory immersion vessel is configured to continuously or intermittently output essential oils, perfumes, or other scent molecules at a digital scent device within sensory immersion vessel during the digital medicine experience (e.g., located within a headset worn by the user or emitted from an actuator within the sensory immersion vessel). In one implementation, the digital scent device is configured to continuously output a small amount of fragrance of a particular scent to produce a subtle background aroma throughout the digital medicine experience. In another implementation, the digital scent device is configured to output fragrance in conjunction with an event within the multi-sensory virtual environment or in conjunction with an object or set of objects entering the multi-sensory virtual environment. In the example of the "crystal cave" experience, the digital scent device can continuously output small amounts of fragrance or other scent molecules to produce a mossy or earthy aroma within the sensory immersion vessel in order to enhance the user's experience of the multi-sensory virtual environment.

Generally, the sensory immersion vessel can synchronize the olfactory representations of these objects or features of the multi-sensory virtual environment with visual, auditory and/or renderings of these elements at other actuators in the sensory immersion vessel in order: to increase the user's sense of immersion in the multi-sensory virtual environment; and to facilitate the user's transition to the target physiological state. Thus, by synchronizing sensory outputs across multiple sensory modalities (e.g., sensory synchronization) and customizing the digital medicine experience to the physiological state of the user according to the closed-loop controls described below, the system can provide effective experiential treatments through which users can achieve a meaningful and sustainable health benefit.

Generally, the system is configured to render movement of visual objects within the multi-sensory virtual environment and/or movement of the user through the multi-sensory virtual environment during the digital medicine experience. The rate of this movement, the rate progression through the multi-sensory virtual environment and/or the rate of progression through the overall digital medicine experience is generally variable and depends on the current physiological state of the user (e.g., relative to the target physiological state for the digital medicine experience). In other words, sensory representations of objections in the multi-sensory virtual environment and the rate at which the user experiences changes in the multi-sensory virtual environment within the sensory immersion vessel are responsive to and dependent on the user's current physiology. Upon initializing the digital medicine experience (e.g., at the initial time or at a later time within the experience). However, the system can determine (e.g., derive, compute, set) an initial rate at which to render progression through the multi-sensory virtual environment and/or the digital medicine experience, which may remain independent of the user's physiological state for a predetermined amount of time. In one variation, the system can render movement of or movement within the multi-sensory virtual environment at a predetermined initial rate by, for example, advancing through (e.g., playing back) a sequence of mixed reality frames representing the multi-sensory virtual environment at this predetermined initial rate. In another variation, the system can calculate an initial rate of progression through the multi-sensory virtual environment and/or the digital medicine experience based on the physiological model of the user and/or a physiological model of the user's demographic. For example, if the user or the user's demographic tends to exhibit high physiological sensitivities to changes in a multi-sensory virtual environment at the beginning of their digital medicine experiences, the system can set (e.g., calculate, compute, determine) a relatively slow initial rate of progression for the current experience in order to customize the digital medicine experience to the user's particular physiology and avoid outsized physiological responses to associated stimuli at the start of the digital medicine experience. In another variation, the system can calculate an initial rate of progression through the multi-sensory virtual environment and/or the digital medicine experience corresponding to the baseline physiological state of the user measured prior to initiating the experience.

In yet another variation, the system can calculate a rate of progression through the multi-sensory virtual environment and/or the digital medicine experience corresponding to the current physiological state of the user thus measured within the experience.

Upon calculating the initial rate of progression for the digital medicine experience, the system can render sensory representations of a set of elements in a multi-sensory virtual environment within the sensory immersion vessel at the corresponding rate of progression. For example, the system can render a set of visual objects within the multi-sensory virtual environment moving at an initial speed corresponding to this initial rate of progression. Additionally and/or alternatively, the system can render (e.g., simulate) movement of the user through the multi-sensory virtual environment at the current rate of progression. In the example of the "crystal cave" experience, displays within the sensory immersion vessel can render the cavern ceiling and associated objects (e.g., crystal formations, stalactites, stalagmites) moving toward the user's point of view at this initial rate of progression to simulate the user floating through the cavern at a particular speed. Simultaneously, fans within the sensory immersion vessel can generate air movement at the head and/or torso sections of the sensory immersion vessel to produce a wind effect proportional to the speed of movement through the cavern.

However, the system can implement any other method or technique to output a multi-channel stimulus presentation that integrates stimulus delivery and real-time experiential control mechanisms with multi-channel data acquisition and analysis in order to allow dynamic control of the experience and stimulus modification based on neural or behavioral responses.

2.5 Closed Loop Algorithms Responsive to Physiological State

Blocks of the second method S200 recite: at a first time during the digital medicine experience, succeeding the initial time, measuring a first value of the first bioindicator at Block S240; calculating a first rate of progression through the digital medicine experience based on a first difference between the first value of the first bioindicator and the target value of the first bioindicator at Block S250; and at a second time succeeding the first time, rendering sensory representations of the set of elements in the multi-sensory virtual environment at the first rate of progression at Block S260. Generally, the system is configured to: continuously and/or intermittently sample values of a bioindicator (e.g., heart rate, respiration rate, brain activity etc.) representative of a current physiological state of the user during the digital medicine experience; dynamically recalculate the rate of progression through the digital medicine experience and/or rate of movement through the multi-sensory virtual environment corresponding to the digital medicine experience based on a current difference between the sampled (e.g., current) value of the bioindicator and the target value of the bioindicator; and to dynamically update the multi-sensory virtual environment to render movement (or appearance) of objects, sensory outputs, and/or movement of the user's point of view within the multi-sensory virtual environment at the newly calculated rate of progression.

Figure 5:
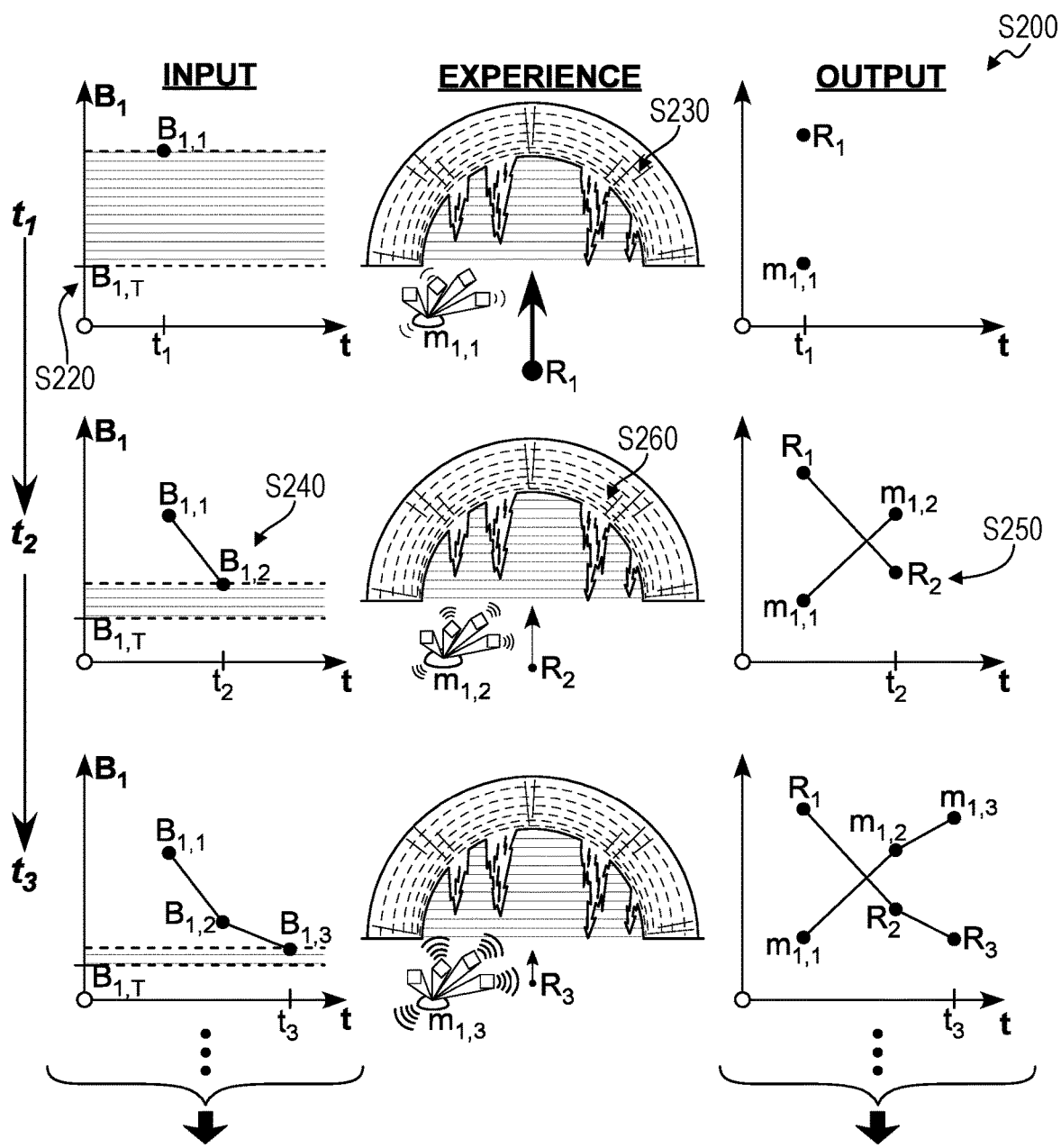
FIG. 5 is a flowchart representation of one variation of the second method.
Figure 5:
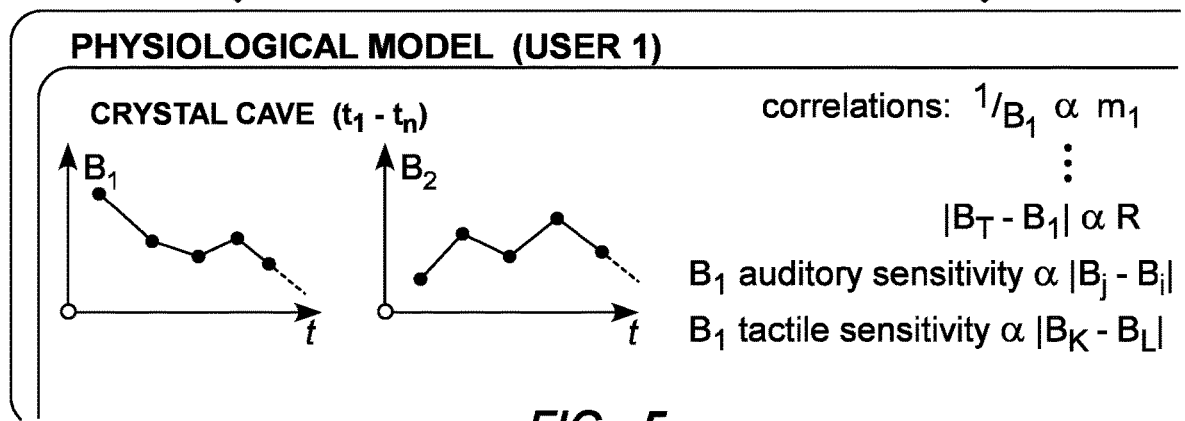

Throughout the digital medicine experience, the system is configured to continuously and/or intermittently sample values of a set of bioindicators representing the physiological state of the user during the experience as illustrated in FIG. 5. For example, the system can recruit a set of sensors within the sensory immersion vessel to continuously sample (e.g., measure, monitor) the user's heart rate, breathing rate, dissolved blood oxygen, galvanic skin response, blood pressure, EKG, EEG, etc. For each digital medicine experience, the system can analyze numerous bioindicators simultaneously (e.g., heart rate, breathing rate, EEG, etc.) and execute machine learning algorithms to interpret the significance of these bioindicators as they relate to the user's overall physiological state (e.g., including neurological/cognitive state) and/or the therapeutic goal or category of the selected digital medicine experience. For example, the system can select heart rate or galvanic skin response (generally metrics of stress response) as a representative bioindicator (e.g., $B_1$ of FIG. 5) for digital medicine experiences in the "relax" category, and select breathing rate (generally a metric of as the representative bioindicator for experiences in the "meditate" category). For example, in the "crystal cave" experience, the system can select heart rate as the first (e.g., representative) bioindicator and dynamically modify sensory parameters of the cave environment and/or the rate of progression through the cave experience based on sampled heart rate values throughout the digital medicine experience, as described in more detail below. As another example, in the "crystal cave" experience, the system can: combine an EEG signal from the user in combination with the user's heart rate; store this result as a cumulative (e.g., or "representative") bioindicator; and dynamically modify sensory parameters of the cave environment and/or the rate of progression through the cave experience based on this cumulative bioindicator (e.g., combined EEG and heart rate values) throughout the digital medicine experience, as described below in order to effect the physiological and cognitive changes within the user.

Subsequently and/or concurrently, the system can define an internal correlation between this representative bioindicator and the rate of progression through or type of sensory stimulation within the digital medicine experience and/or multi-sensory virtual environment such that the rate at which sensory parameters of elements in the multi-sensory virtual environment is both dependent on and responsive to the physiological state of the user (e.g., relative to the target physiological state). In particular, after rendering changes in the multi-sensory virtual environment at the initial rate of progression for the digital medicine experience (e.g., for a predetermined period of time), the system can sample values (e.g., first value) of the representative bioindicators (e.g., heart rate, breathing rate, etc.) at sensors within the sensory immersion vessel. The system is configured to then calculate a difference between the sampled value and the target value of the representative bioindicators and then derive (e.g., calculate, compute, set) a current (e.g., updated) rate of progression for the digital medicine experience based on the difference between the sampled and target values. The system can then modify sensory parameters or render movement of the multi-sensory virtual environment at the current (e.g., updated) rate of progression as shown in FIG. 5. For example, the sensory immersion vessel can update the rendering of a set of visual objects such that the visual objects move at a speed corresponding to the current rate of progression rather than the initial rate of progression. In other words, the system can change the overall rate of progression through the digital medicine experience, the rate of an object's movement (or appearance) within and/or rate of movement of the user's point of view through the multi-sensory virtual environment from the initial rate of progression to the updated rate of progression in response to detecting a difference between the sampled (e.g., current) value of the representative bioindicator and the target value of the representative bioindicator. For example, shortly after initializing the "crystal cave" experience, the sensory immersion vessel can sample a value of the user's heart rate and/or breathing rate at an integrated heart rate monitor and/or breathing rate monitor (e.g., a thermocouple or pulse oximeter contained within the headset). The system can then determine a difference between the sampled heart rate and/or breathing rate and the target heart rate and/or breathing rate set prior to initializing the experience (e.g., sampled at 75 BPM vs. target of 65 BPM) and calculate a new progression rate at which the user's point of view moves through the cave that is based on (e.g., proportional to) this difference. The system can then adjust its rendering of the multi-sensory cave environment to change the speed at which the user's point of view drifts (e.g., moves) through the cave according to the newly calculated progression. For example, the sensory immersion vessel can render movement through the multi-sensory cave environment at a speed that is slower than initial speed at the start of the experience. In one implementation, the system can then adjust its rendering of the multi-sensory cave environment to change the appearance or shape of objects within the virtual environment based on the user's current and/or target bioindicator values, as described in more detail below.

As shown in FIG. 5, the system is configured to dynamically recalculate the rate of progression through the digital medicine experience, rate of progression through the multi-sensory virtual environment, and/or rate of movement as well as appearance of objects within the environment throughout the course of the digital medicine experience responsive to observed changes in the user's physiological state. In particular, the system is configured to subsequently recalculate a new rate of progression in response to detecting further changes in the difference between the measured values of the representatives bioindicators and the target values of the representative bioindicators. For example, after adjusting the rate of progression as described above, the system can: sample a second value of the representative bioindicator; calculate a second rate of progression through the digital medicine experience based on the difference between the second value of the first bioindicator and the target value of the representative bioindicator; and subsequently render sensory representations of the set of elements in the multi-sensory virtual environment at the second rate of progression by, for example, rendering movement of a set of visual objects in the multi-sensory virtual environment at a second speed corresponding to the second rate of progression. In the example of the "crystal cave" experience, the system can once again sample the user's heart rate and compare this value to the target heartrate (e.g., 70 BPM vs. 65 BPM). The system will then calculate an updated rate of progression proportional to the new difference in heart rate and update its rendering of the multi-sensory cave environment accordingly. For example, the system can further reduce the user's perceived speed of movement through the cave environment by rendering movement of the cavern ceiling and associated objects at a slower speed and simultaneously reducing the speed of air movement through the sensory immersion vessel to match the reduced movement speed of these visual objects. In one implementation, the system can also modify sensory representations of objects within the virtual environment (e.g., the rate of pulsation or luminosity) to match the speed of air movement (or other sensory output) within the sensory immersion vessel.

Furthermore, the system can correlate observed changes in the value representative bioindicators with changes in the rate of progression and/or appearance of objects throughout the digital medicine experience. In other words, the system can associate changes in the rate of progression through and/or appearance of objects within the multi-sensory virtual environment and/or digital medicine experience with observed movement in the representative bioindicators toward the target values and account for this correlation when calculating future adjustments to the rate of progression and/or future adjustments of other sensory parameters of the multi-sensory virtual environment in order to guide the representative bioindicator's value toward the target state. In the "crystal cave" example, the system may correlate the observed 5 BPM decrease in the user's heart rate with its previous reduction in the speed of simulated movement through the cave environment. The system can then further decrease this movement speed (e.g., rate of progression) through the cave environment or modify the visual and/or sensory parameters of various objects within the virtual environment when recalculating the rate of progression and/or sensory parameters of various objects within the virtual environment at a later time in order to guide the user toward her target heart rate for the experience.

The system can thus dynamically recalculate a new rate of progression for the digital medicine experience based on the changes in the user's physiological state and modify sensory representations of the multi-sensory virtual environment accordingly in real-time, which may occur many (e.g., dozens, hundreds) times resulting in a "closed loop" mixed reality experience that both responds to and implicitly influences the physiological and/or cognitive state of the user in order to gradually transition the representative bioindicator from its baseline value (e.g., at the beginning of the experience) or current value to the target value by the end of the digital medicine experience.

In one variation, the target physiological state defines multiple target values (e.g., physiological metrics) for multiple different representative bioindicators. For example, the target physiological state can include a heart rate of 65 BPM and a breathing rate of ten cycles per minute. In this variation, the system can calculate the rate of progression through the digital medicine experience, the rate of progression through the multi-sensory virtual environment and/or rate of movement of visual objects in the multi-sensory virtual environment based on differences (and/or correspondences) between sampled and target values of any of these representative bioindicators. The system can also calculate the rate of progression based on different bioindicators at different times during the digital medicine experience. In particular, after calculating a first rate of progression based on a first bioindicator, the system is configured to: calculate a target value of a second bioindicator of the physiological state of the user, the target value of the second bioindicator also defining the target physiological state of the user; sample a value of the second bioindicator; calculate a second rate of progression through the digital medicine experience based on a difference between the first value of the second bioindicator and the target value of the second bioindicator; and subsequent sensory representations of the set of elements in the multi-sensory virtual environment at the second rate of progression. In one example, the system can switch to calculating the rate of progression based on the second representative bioindicator upon detecting that the first bioindicator has reached its target value. For instance, if the system detects that the user's heart rate has reached the target value of 65 BPM, the system can base subsequent changes to the rate of progression on the difference between the user's observed rate of respiration and the target rate of respiration. In another example, the system can switch to calculating the rate of progression based on the second representative bioindicator in response to a rendering a particular event or substantial change in the multi-sensory virtual environment (e.g., transitioning the user's point of view to a new area of the cave environment). In another example, the system can switch to calculating the rate of progression based on the second indicator in response to rendering a particular object entering or exiting the visual scene in the multi-sensory virtual environment. In yet another example, the system can switch to calculating the rate of progression based on the algorithmic correspondence (e.g., as determined by a machine learning algorithm) between multiple bioindicators in response to rendering a particular object entering or exiting the visual scene in the multi-sensory virtual environment. Thus, the system is generally configured to execute a process similar to Blocks S240, S250, and S260 for multiple different bioindicators during the digital medicine experience (e.g., in order to guide the user toward a target physiological state that includes multiple bioindicator targets).

In addition to dynamically adjusting the overall rate of progression for the digital medicine experience, the system is also configured to correlate sensory representations of objects in the multi-sensory virtual environment and/or sensory parameters of the multi-sensory virtual environment with sampled values of a particular bioindicator, thereby synchronizing output sensory stimuli with the user's current physiology. In particular, the system can adjust the magnitude of a particular sensory output or a sensory representation of an object in the multi-sensory virtual environment in a manner proportional to the current (e.g., sampled) value of a bioindicator. For example, in the "crystal cave" experience, the sensory immersion vessel can render the crystal formations within the cave to pulse with light at a rate proportional to the user's current heart rate (e.g., alternately illuminate the crystals over a first number of heartbeats and dim the crystals over the next number of heartbeats). Alternatively and/or additionally, the sensory immersion vessel can produce air movement at the set of fans located in the head and torso sections of the sensory immersion vessel at a speed proportional to the user's breathing rate (e.g., reduce the simulated speed of wind though the cave as the user reduces her breathing rate). In one implementation, the system can calculate both the rate of progression through the digital medicine experience and sensory output magnitudes of particular objects or features in the multi-sensory virtual environment based on values of the same bioindicator. In another implementation, the system can calculate the rate of progression based on values of a first bioindicator, and calculate sensory output magnitudes based on a values of a second, different bioindicator. Thus, the system can represent sensory mappings of a bioindicator or set of bioindicators within the multi-sensory virtual environment that are perceptible to the user and control and/or modify these sensory representations (e.g., a sensory output magnitude) in response to the changes in the associated bioindicators in order to: customize the multi-sensory virtual environment to the user's physiological state; increase the user's immersion in the multi-sensory virtual environment; and implicitly guide the user toward the target physiological state through closed-loop control of these sensory mappings. Therefore, by customizing the digital medicine experience to the physiological state of the user according to these closed-loop controls and synchronizing sensory outputs across multiple sensory modalities (e.g., sensory synchronization), the system can deliver experiential treatments through which the user may achieve a meaningful and sustainable health benefit.

More specifically, during the digital medicine experience, the system can: sample a value of a bioindicator; calculate a difference between the sampled value of the bioindicator and the target value of the bioindicator; and in response to determining that the second difference is less than the first difference, correlate the difference between the first value of the first bioindicator and the second value of the first bioindicator with the first sensory output magnitude, and render sensory representations of the set of elements in the multi-sensory virtual environment at a second sensory output magnitude that is less than the first sensory output magnitude. In other words, the system can dynamically recalculate the magnitude of sensory output for one or more objects or features in the multi-sensory virtual environment to match the current value of a particular bioindicator (e.g., heart rate) and/or the cumulative values of several bioindicators (breathing rate, EEG, etc.). The system therefore generates a closed feedback loop in which sensory representations of these objects and/or features of the multi-sensory virtual environment are responsive to and can also influence the physiological state of the user (e.g., similar to the closed loop control of the rate of progression described above). The system can further correlate any observed changes in the value of the bioindicator and/or movement of the bioindicator value toward the target value with changes in the sensory output magnitude of objects or features in the multi-sensory virtual environment. In the example of the "crystal cave" experience, the system may detect that the user's breathing rate has reduced after changing the speed of air movement within the sensory immersion vessel. The system can then correlate this reduction in the user's breathing rate with the rate of air movement and further reduce the rate of air movement at a later time in order to guide the user's rate of respiration toward its target value. Alternatively, the system can increase the sensory output magnitude of objects or features in the multi-sensory virtual environment (e.g., for an experience in the "restore" category). Similar to the dynamic adjustment of the rate of progression described above, the system can update sensory output magnitudes and sensory representations of objects many times (e.g., dozens of times, hundreds of times) throughout the digital medicine experience in response to changes in a biosignal or set of biosignals in order to deliver an experience that is partially controlled by and responsive to the user's physiological state.

In one variation, in response to detecting that the user has reached the target physiological state and/or sustained the target physiological state, the system can gradually increase the overall sensory output magnitudes within the multi-sensory virtual environment while monitoring values of a representative bioindicator, which can condition the user (e.g., over the course of multiple experiences) to maintain a relaxed physiological state when presented with increased sensory stimuli. In particular, in response to detecting that the user has reached and/or maintained the target physiological state, the system can: increase the sensory output magnitude of sensory representations of elements within the multi-sensory virtual environment; sample a value of a representative bioindicator; and, in response to determining that the sampled value of the bioindicator is within a threshold of the target value of the representative bioindicator, further increase the sensory output magnitude of these elements. Alternatively and/or additionally, in response to detecting that the sampled value of the bioindicator exceeds the target value of the bioindicator by a particular threshold, the system can reduce the sensory output magnitude in order to maintain the target physiological state of the user. Thus, the system can gradually increase or decrease the level of sensory stimulus in the multi-sensory virtual environment after the user has attained the target state while monitoring a biosignal to ensure that the user's physiological state remains close to the target physiological state. During the course of a single experience (or over the course of multiple digital medicine experiences), the system can therefore condition the user to remain relaxed and calm (e.g., as indicated by heart rate, galvanic skin response, breathing rate etc.) even under increasing sensory stimulation, which can decrease anxiety and/or or stress responses in real-world settings and environments.

However, the system can implement any method, technique, or closed-loop controls to control the experience according the user's physiological state, improve the user experience by analyzing user biodata and modifying output parameters, and/or improve efficacy and stability of these control mechanisms in the sensory immersion vessel based on changes in the user's biosignals responsive to output signals of the sensory immersion vessel.

2.6 Modeling

Generally, the system is configured to generate a physiological model of the user during the digital medicine experience based on the user's physiological state throughout the experience and the user's physiological reactions to certain stimuli, events, and/or objects in the multi-sensory virtual environment. The physiological model can include time series representations of bioindicator values sampled throughout the digital medicine experience and sensitivities of the user to classes of stimuli (e.g., visual, auditory, tactile, olfactory). The system can then leverage this physiological model to predict the effect of particular events or stimuli that occur during the digital medicine experience or during subsequent digital medicine experiences in order to adjust sensory parameters of the experience and/or the rate of progression through the experience to affect the physiological state of the user consistent with the therapeutic goals of the experience.

In one variation, the system is configured to determine physiological sensitivities of the user to various categories of sensory stimuli (e.g., visual, auditory, olfactory, tactile) in response to output controlled stimuli and/or events within the multi-sensory virtual environment during the digital medicine experience. In particular, the system is configured to, at a first time during the digital medicine experience: sample a value of a representative bioindicator; after sampling the bioindicator value, subsequently output audio signals at a set of speakers within the sensory immersion vessel; subsequently sample a second value of the representative bioindicator; and calculate a sensitivity of the representative bioindicator to auditory stimuli based on the difference between the sampled values. The system is also configured to, at a second time during the digital medicine experience: sample a value of a representative bioindicator; after sampling the bioindicator value, subsequently output tactile feedback at a set of actuators within the sensory immersion vessel; subsequently sample a second value of the representative bioindicator; and calculate a sensitivity of the representative bioindicator to tactile stimuli based on the difference between the sampled values. The system is also configured to, at a third time during the digital medicine experience: sample a value of a representative bioindicator; after sampling the bioindicator value, subsequently output an olfactory signal at a digital scent device within the sensory immersion vessel; subsequently sample a second value of the representative bioindicator; and calculate a sensitivity of the representative bioindicator to olfactory stimuli based on the difference between the sampled values. The system can therefore sample values of a bioindicator (e.g., heart rate, galvanic skin response, breathing rate) before and after the output of a controlled sensory stimulus in order to determine a user's physiological sensitivity (e.g., as measured by a particular signal) to each type of stimulus in the multi-sensory environment. The system can execute this method multiple times (e.g., for each bioindicator in a set of bioindicator) to generate a detailed physiological model of the user's sensitivities to various types of stimuli. As shown in FIG. 5, the system can then store these sensitivities alongside time series representations of values of each bioindicator sampled during the digital medicine experience in a physiological model of the user, which can be used to predict the user's physiological responses to sensory stimuli, events within and features of the multi-sensory virtual environment, changes in the rate of progression of the digital medicine experience, etc. The system can also derive correlations between this set of bioindicators and other sensory parameters of the digital medicine experience as described above (e.g., rate of progression through the multi-sensory virtual environment, sensory output magnitudes related to particular objects in the multi-sensory virtual environment) and store derived correlations in the physiological model of the user. The system can determine modifications to sensory parameters of the multi-sensory virtual environment and adjustments to the rate of progression through as well as appearance of objects within the digital medicine experience in real time based on these predicted physiological responses in order to more effectively guide the user toward the target physiological state—such as including neurological and/or cognitive changes—during the digital medicine experience or in subsequent digital medicine experiences according to unique physiological qualities of the user as observed by the sensory immersion vessel.

The systems and methods described herein can be embodied and/or implemented at least in part as a machine configured to receive a computer-readable medium storing computer-readable instruction. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instruction. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

I claim:

1. A method for delivering a digital medicine experience responsive to a physiological state of a user of a sensory immersion vessel, comprising:
   loading data of the digital medicine experience into a computer system of the sensory immersion vessel;
   calculating a target value of a first bioindicator of the physiological state of the user, the target value of the first bioindicator corresponding to a target physiological state of the user;
   at an initial time, rendering sensory representations of a set of elements in a multi-sensory virtual environment within the sensory immersion vessel at an initial rate of progression;
   at a first time during the digital medicine experience, succeeding the initial time, sampling a first value of the first bioindicator;
   calculating a first rate of progression through the digital medicine experience based on a first difference between the first value of the first bioindicator and the target value of the first bioindicator; and
   at a second time succeeding the first time, rendering the sensory representations of the set of elements in the multi-sensory virtual environment at the first rate of progression, which comprises:
   - rendering a set of visual objects in the multi-sensory virtual environment at a display within the sensory immersion vessel;
   - outputting a set of auditory signals corresponding to a first subset of the set of visual objects at a set of speakers within the sensory immersion vessel;
   - outputting tactile representations of a second subset of the set of visual objects at a set of actuators within the sensory immersion vessel; and
   - outputting olfactory representations of a third subset of the set of visual objects at a digital scent device within the sensory immersion vessel.

2. The method of claim 1, further comprising:
   at a third time succeeding the second time during the digital medicine experience, sampling a second value of the first bioindicator;
   calculating a second rate of progression through the digital medicine experience based on a second difference between the second value of the first bioindicator and the target value of the first bioindicator; and
   at a fourth time succeeding the third time, rendering the sensory representations of the set of elements in the multi-sensory virtual environment at the second rate of progression.

3. The method of claim 1, further comprising:
   calculating a target value of a second bioindicator of the physiological state of the user, the target value of the second bioindicator corresponding to the target physiological state of the user;
   at a third time succeeding the second time during the digital medicine experience, sampling a first value of the second bioindicator;
   calculating a second rate of progression through the digital medicine experience based on a difference between the first value of the second bioindicator and the target value of the second bioindicator; and
   at a fourth time succeeding the third time, rendering the sensory representations of the set of elements in the multi-sensory virtual environment at the second rate of progression.

4. The method of claim 3:
   wherein rendering sensory representations of the set of elements in the multi-sensory virtual environment at the initial rate of progression comprises rendering the set of visual objects moving at an initial speed, corresponding to the initial rate of progression, within the multi-sensory virtual environment;
   wherein rendering sensory representations of the set of elements in the multi-sensory virtual environment at the first rate of progression comprises rendering the set of visual objects moving at a first speed, corresponding to the first rate of progression, within the multi-sensory virtual environment; and
   wherein rendering sensory representations of the set of elements in the multi-sensory virtual environment at the second rate of progression comprises rendering movement of the set of visual objects at a second speed corresponding to the second rate of progression.

5. The method of claim 1:
   wherein rendering the set of visual objects in the multi-sensory virtual environment comprises rendering visual representations of a cave ceiling and embedded crystal formations above a body of water within the sensory immersion vessel;

wherein outputting the set of auditory signals corresponding to the first subset of the set of visual objects comprises playing back an audio representation of wind at the set of speakers within the sensory immersion vessel;

wherein outputting the tactile representations of the second subset of the set of visual objects comprises generating air movement at a set of fans within the sensory immersion vessel; and wherein outputting the olfactory representations of the subset of the set of visual objects comprises outputting a scented perfume at the digital scent device within the sensory immersion vessel.

6. The method of claim 1, further comprising:
at a third time, succeeding the first time, sampling a second value of the first bioindicator;
at approximately the third time, outputting a second set of auditory signals at the set of speakers;
after outputting the second set of auditory signals, sampling a third value of the first bioindicator;
calculating a second difference between the third value of the first bioindicator and the second value of the first bioindicator; and
calculating a sensitivity of the first bioindicator to auditory stimuli based on the second difference.

7. The method of claim 6, further comprising:
at a fourth time, succeeding the first time, sampling a fourth value of the first bioindicator;
at approximately the fourth time, outputting a tactile signal at the set of actuators;
after outputting the tactile signal, sampling a fifth value of the first bioindicator;
calculating a third difference between the fifth value of the first bioindicator and the fourth value of the first bioindicator; and
calculating a sensitivity of the first bioindicator to tactile stimuli based on the third difference.

8. The method of claim 7, further comprising:
at a fifth time, succeeding the first time, sampling a sixth value of the first bioindicator;
at approximately the fifth time, outputting an olfactory signal at the digital scent device;
after outputting the olfactory signal, sampling a seventh value of the first bioindicator;
calculating a fourth difference between the seventh value of the first bioindicator and the sixth value of the first bioindicator; and
calculating a sensitivity of the first indicator to olfactory stimuli based on the fourth difference.

9. The method of claim 8, further comprising:
arranging the first, second, third, fourth, fifth, and sixth values of the first bioindicator into a time series representing values of the first bioindicator throughout the digital medicine experience;
storing the time series representing the first bioindicator in a user profile; and
storing the sensitivity of the first bioindicator to auditory stimuli, the sensitivity of the first bioindicator to tactile stimuli, and the sensitivity of the first bioindicator to olfactory stimuli in the user profile.

10. The method of claim 9, further comprising:
loading a second digital medicine experience for the user at the sensory immersion vessel;

calculating a second target value of the first bioindicator corresponding to the second digital medicine experience based on the time series representing the first bioindicator, the second target value of the first bioindicator corresponding to a second target physiological state; and
calculating a second initial rate of progression for the second digital medicine experience based on the time series representing the first bioindicator, the sensitivity to auditory stimuli, the sensitivity to tactile stimuli, and the sensitivity to olfactory stimuli.

11. The method of claim 1, further comprising, at the second time, rendering the sensory representations of the set of elements in the multi-sensory virtual environment at a first sensory output magnitude proportional to the first value of the first bioindicator.

12. The method of claim 11, wherein rendering sensory representations of the set of elements in the multi-sensory virtual environment at the first sensory output magnitude proportional to the first value of the first bioindicator comprises rendering movement of the set of visual objects in the multi-sensory virtual environment at a rate proportional to a heart rate of the user.

13. The method of claim 12, wherein rendering movement of the set of visual objects in the multi-sensory virtual environment comprises illuminating a set of crystal formations within a cave at a second rate proportional to the heart rate of the user.

14. The method of claim 12, wherein rendering sensory representations of the set of elements in the multi-sensory virtual environment at the first sensory output magnitude proportional to the first value of the first bioindicator comprises modulating a rate of air movement within the sensory immersion vessel proportional to a rate of respiration of the user.

15. The method of claim 11, further comprising:
at a third time, succeeding the second time, measuring a second value of the first bioindicator;
calculating a second difference between the second value of the first bioindicator and the target value of first bioindicator; and
in response to determining that the second difference is less than the first difference:
- correlating a third difference between the first value of the first bioindicator and the second value of the first bioindicator with the first sensory output magnitude, and
- rendering the sensory representations of the set of elements in the multi-sensory virtual environment at a second sensory output magnitude that is less than the first sensory output magnitude.

16. The method of claim 15, further comprising:
at a fourth time, succeeding the third time, measuring a third value of the first bioindicator;
calculating a fourth difference between the third value of the first bioindicator and the target value of the first bioindicator; and
in response to determining that the fourth difference is less than the second difference:
- correlating a fifth difference between the third value of the first bioindicator and the second value of the first bioindicator with a sixth difference between the first sensory output magnitude and the second sensory output magnitude, and
- rendering the sensory representations of the set of elements in the multi-sensory virtual environment at a third sensory output magnitude that is less than the second sensory output magnitude.

17. The method of claim 11, further comprising: at a third time, succeeding the second time, sampling a second value of the first bioindicator;
- calculating a second difference between the second value of the first bioindicator and the target value of the first bioindicator;
- in response to determining that the second difference is less than the first difference:
  - ■ correlating a third difference between the first value of the first bioindicator and the second value of the first bioindicator with the first sensory output magnitude, and
- rendering the sensory representations of the set of elements in the multi-sensory virtual environment at a second sensory output magnitude that is greater than the first sensory output magnitude.

18. The method of claim 11, further comprising:
- in response to detecting that the user has sustained the target physiological state of the user for a predetermined duration: rendering the sensory representations of the set of elements in the multi-sensory virtual environment at a second sensory output magnitude greater than the first sensory output magnitude;
- sampling a second value of the first bioindicator; and
- determining that a second difference between the second value of the first bioindicator and the target value of the first bioindicator falls below a threshold difference, and, in response, rendering the sensory representations of the set of elements in the multi-sensory virtual environment at a third sensory output magnitude greater than the second sensory output magnitude.

19. The method of claim 1, further comprising:
- at the second time, rendering the sensory representations of the set of elements in the multi-sensory virtual environment at a first sensory output magnitude proportional to a first value of a second bioindicator different from the first bioindicator.

* * * * *